United States Patent
Velagapudi et al.

(10) Patent No.: US 12,357,645 B2
(45) Date of Patent: Jul. 15, 2025

(54) DRUG COMBINATION FOR TREATMENT OF GASTRIC CANCER

(71) Applicant: MINNEAMRITA THERAPEUTICS LLC, Tampa, FL (US)

(72) Inventors: Mohana R. Velagapudi, Tampa, FL (US); Ashok Kumar Saluja, Tampa, FL (US)

(73) Assignee: Minneamrita Therapeutics LLC, Tampa, FL (US)

(*) Notice: Subject to any disclaimer, the term of this patent is extended or adjusted under 35 U.S.C. 154(b) by 0 days.

(21) Appl. No.: 18/721,770

(22) PCT Filed: Mar. 8, 2024

(86) PCT No.: PCT/US2024/019195
§ 371 (c)(1),
(2) Date: Jun. 19, 2024

(87) PCT Pub. No.: WO2024/187139
PCT Pub. Date: Sep. 12, 2024

(65) Prior Publication Data
US 2024/0415856 A1    Dec. 19, 2024

Related U.S. Application Data

(63) Continuation-in-part of application No. PCT/US2023/015809, filed on Mar. 21, 2023.

(60) Provisional application No. 63/489,205, filed on Mar. 9, 2023.

(51) Int. Cl.
A61K 31/665 (2006.01)
A61K 31/337 (2006.01)
A61P 35/00 (2006.01)

(52) U.S. Cl.
CPC .......... *A61K 31/665* (2013.01); *A61K 31/337* (2013.01); *A61P 35/00* (2018.01)

(58) Field of Classification Search
CPC .................................................. A61K 31/665
See application file for complete search history.

(56) References Cited

U.S. PATENT DOCUMENTS

| | | |
|---|---|---|
| 8,507,552 B2 | 8/2013 | Georg et al. |
| 9,150,600 B2 | 10/2015 | Georg et al. |
| 9,623,035 B2 | 4/2017 | Georg et al. |
| 10,328,050 B2 | 6/2019 | Astsaturov et al. |
| 10,695,319 B2 | 6/2020 | Liu et al. |
| 10,709,725 B2 | 7/2020 | Li |
| 11,007,194 B2 | 5/2021 | Stuart et al. |
| 11,306,070 B2 | 4/2022 | Gray et al. |
| 2007/0092585 A1 | 4/2007 | Skinner |
| 2011/0045102 A1 | 2/2011 | Skinner |
| 2019/0133963 A1 | 5/2019 | Kharbanda et al. |
| 2019/0321305 A1 | 10/2019 | Kharbanda et al. |
| 2020/0071415 A1 | 3/2020 | Cronier et al. |
| 2020/0297693 A1 | 9/2020 | Liu et al. |
| 2021/0000778 A1 | 1/2021 | Luther et al. |
| 2021/0196730 A1 | 7/2021 | Qian et al. |
| 2021/0205286 A1 | 7/2021 | Deretic et al. |
| 2021/0267922 A1 | 9/2021 | Luther et al. |
| 2023/0038138 A1 | 2/2023 | Hattersley et al. |

FOREIGN PATENT DOCUMENTS

| | | |
|---|---|---|
| CN | 105434446 A | 3/2016 |
| CN | 111032043 A | 4/2020 |
| CN | 112839675 A | 5/2021 |
| WO | 2020023439 A1 | 1/2020 |

OTHER PUBLICATIONS

Lee et al., Phase I study of Minnelide and paclitaxel combination therapy in refractory gastric cancer (GC). Journal of Clinical Oncology, vol. 41, No. 4, supl, Feb. 2023, Meeting Abstract: 2023 ASCO Gastrointestinal Cancers Symposium, Jan. 24, 2023.*
Clinical Trial NCT03129139, A Phase 1, Multi-Center, Open-Label, Dose-Escalation, Safety, Pharmacokinetic, and Pharmacodynamic Study of Minnelide™ Capsules Given Alone or in Combination With Protein-Bound Paclitaxel in Patients With Advanced Solid Tumors (Minnelide 101), updated on Apr. 4, 2022, available at http.*
Lim et al., The safety and efficacy outcomes of Minnelide given alone or in combination with paclitaxel in advanced gastric cancer: A phase I trial, Cancer Letters, vol. 597, Aug. 10, 2024, 217041.*
Borazanci et al., "First-in-Human Phase I Study of Minnelide in Patients With Advanced Gastrointestinal Cancers: Safety, Pharmacokinetics, Pharmacodynamics, and Antitumor Activity," The Oncologist, 29, 132-14, Jan. 2024.
Clinical Trial NCT03129139, A Phase 1, Multi-Center, Open-Label, Dose-Escalation, Safety, Pharmacokinetic, and Pharmacodynamic Study with Protein-Bound Paclitaxel in Patients with Advanced Solid Tumors (Minnelide 101), Retrieved from https://beta.clinicaltrials.gov/study/NCT03129139; 12pgs, Apr. 6, 2022.

(Continued)

*Primary Examiner* — Svetlana M Ivanova
(74) *Attorney, Agent, or Firm* — Haukaas Fortius PLLC; Michael Haukaas

(57) ABSTRACT

A gastric cancer therapy dosing regimen that results in enhanced therapeutic effectiveness and reduced side effects has been discovered. Gastric cancer patients treated daily with a combination of minnelide prodrug and paclitaxel experienced significant negative side effects and progression of the cancer. A minnelide prodrug and paclitaxel combination therapy administered according to a novel dosing regimen provided significantly improved treatment results. The novel dosing regimen comprises a 28-day cycle wherein minnelide prodrug was dosed once per day on days 1 to 5, 8 to 12, and 15 to 19 of the cycle, and paclitaxel was dosed once per day on days 1, 8, and 15 of the cycle. The novel dosing regimen was shown to be both effective toward treating gastric cancer and was well tolerated in human patients.

15 Claims, 16 Drawing Sheets

(56) References Cited

OTHER PUBLICATIONS

International Search Report and Written Opinion of the ISA/EP dated Jun. 10, 2024 in International Application No. PCT/US2024/019195; 14pgs.

International Search Report and Written Opinion of the ISA/US dated Jul. 6, 2023 in International Application No. PCT/US2023/015809; 7pgs.

Lee et al., "Phase I study of Minnelide and paclitaxel combination chemotherapy in refractory gastric cancer (GC)", Journal of Clinical Oncology 41, No. 4, p. 414, Feb. 1, 2023.

Modi et al., "Minnelide synergizes with conventional chemotherapy by targeting both cancer and associated stroma components in pancreatic cancer," Manuscript published as Cancer Letters, vol. 537, 215591, Jul. 2022.

Modi et al., "Triptolide in Combination with Low Dose Gemcitabine and Nab-Paclitaxel: A Novel Effective Combination Chemotherapy Regiment for Pancreatic Cancer," Scientific Forum: 2016 Clinical Congress., vol. 223, No. 4S2, e49, Oct. 2016.

Wang et al., "The enhanced antitumor effect of combined triptolide and paclitaxel on pancreatic cancer call lines," J. Clin. Oncol., 32, 335-335, Jan. 2014.

Zeng et al., "Pharmacological activity and clinical progress of Triptolide and its derivatives LLDT-8, PG490-88Na, and Minnelide: a narrative review," Eur. Rev. Med. Pharmacol. Sci., 27(21): 10181-10203, Nov. 2023.

Park et al., "A phase 1b, open-label, safety, pharmacokinetic, and pharmacodynamic study of an anti super-enhancer triptolide analogue with nab-paclitaxel plus gemcitabine in patients with metastatic adenocarcinoma of the pancreas," Journal of Clinical Oncology., vol. 41, No. 4 suppl., Meeting Abstract, pTPS769, Feb. 2023.

\* cited by examiner

DRUG COMBINATION FOR TREATMENT OF GASTRIC CANCER

RELATED APPLICATIONS

This application is a National Stage filing under 35 U.S.C. § 371 of International Application No. PCT/US2024/019195 filed Mar. 8, 2024, which is a Continuation-in-Part of International Application No. PCT/US2023/015809 filed Mar. 21, 2023, which claims the benefit of U.S. Provisional Patent Application No. 63/489,205 filed Mar. 9, 2023, which applications are incorporated herein by reference.

BACKGROUND OF THE INVENTION

Triptolide, a diterpene isolated from a Chinese medicinal herb, has potent antitumor, immunosuppressive, and anti-inflammatory properties. However, its clinical potential is greatly hampered by limited aqueous solubility and oral bioavailability, and multi-organ toxicity. The prodrug Minnelide™ (14-O-phosphonooxymethyltriptolide disodium salt) is a prodrug that is rapidly converted to triptolide when exposed to phosphatases in the bloodstream. Minnelide prodrug has greater aqueous solubility and less organ toxicity than triptolide. Triptolide has been shown to inhibit tumor cell proliferation and induce apoptosis in vitro and in animal models of cancer, including human mammary tumors (Shamon et al., *Cancer Lett.* 1997; 112:113-117), cholangiocarcinoma cells (Tengchaisri et al., *Cancer Lett.* 1998; 133:169-175), xenografts of several different tumor types, including melanoma, breast cancer, bladder cancer, gastric carcinoma (Yang et al., *Mol Cancer Ther.* 2003; 2:65-72), pancreatic tumors (Phillips et al., *Cancer Res.* 2007; 67 (19): 9407-9416) and neuroblastoma (Antonoff et al, Surgery. 2009; 146:282-290). The greater aqueous solubility of minnelide prodrug compared to triptolide is beneficial for controlling the dosage and safety of the drug.

The antitumor effect of triptolide is the result of inhibition of heat shock protein (HSP) 70 expression in tumor cells and induction of apoptosis. While the mechanism of action of triptolide inhibition of HSP70 expression has not been fully elucidated, it has been shown to induce caspase activation (Choi et al., *Biochem Pharmacol.* 2003; 66:273-280; Liu et al., *Biochem Biophys Res Commun.* 2004; 319:980-6; Wang et al., *J Mol Med.* 2006; 84:405-15; Carter et al, *Blood.* 2006; 108:630-637).

In gastric cancer, triptolide has been shown to inhibit cell growth and induce apoptosis by stimulating the expression of p53 and p21 (waf1/cip1) (Jiang et al., *Oncogene.* 2001 Nov. 29; 20 (55): 8009-18). Triptolide was also shown to be effective in inhibiting colony formation as well as tumor regression in animal models (Yang et al., *Mol Cancer Ther.* 2003; 2:65-72). Other studies have also shown that triptolide inhibits NF-kB in gastric cancer thereby inducing cell death (Chang et al., *Anticancer Res.* 2007 September-October; 27 (5A): 3411-7). Minnelide prodrug, the water-soluble prodrug of triptolide, inhibits Sp1 to decrease HSP70 and induce cell death in gastric cancer cell lines MKN28 and MKN45 (Arora et al., *PLoS One.* 2017 Feb. 13; 12 (2): e0171827). Sp1 is a transcription factor that regulates a number of pro-survival pathways like HSF1. Inhibition of Sp1 transcriptional ability downregulates HSF1 activity thereby decreasing HSP70 and inducing cell death (Arora et al., *PLoS One.* 2017 Feb. 13; 12 (2): e0171827).

Minnelide prodrug, when "activated" by concurrent incubation with alkaline phosphatase, was determined to be as potent as triptolide with respect to decreasing viability of pancreatic tumor cell lines in vitro. "Activated" minnelide prodrug also reduced the proliferation of ovarian carcinoma cells in vitro in a concentration-dependent manner (50-200 nM). Daily intraperitoneal administration of minnelide prodrug at a dose of both 0.2 mg/kg as well as 0.4 mg/kg resulted in markedly decreased tumor weights and volumes in subcutaneous gastric cancer models using cell lines MKN45, MKN28I-N-87.

Combination therapy is a therapeutic intervention in which more than one therapy is administered to a patient. Examples of combination therapy include treatment regimens that involve administering several separate pills, each containing a particular drug, or single pills that contain several drugs. For example, immunotherapy plus chemotherapy. One example is to treat breast or pancreatic cancer with a mix of immunotherapy and chemotherapy drugs such as cisplatin and taxol. A combination of 0.2 mg/kg minnelide prodrug with 100 mg/kg irinotecan was found to be more effective in regressing subcutaneous NCO-N-87 tumors compared to either drug alone in mouse model of gastric cancer.

Taken together, the results of the minnelide prodrug pharmacology program demonstrate that minnelide prodrug has potent antitumor activity against pancreatic, gastric and ovarian tumor cells in vitro (when "activated" with alkaline phosphatase to release triptolide) and markedly improved animal survival and significantly reduced tumor volumes and weights when administered by the oral or IP route either alone or in combination with various "standard of care" agents in models of pancreatic and ovarian cancer. These results support the rationale for evaluation of minnelide prodrug in cancer patients as an individual agent or in combination with other therapies.

As clinical development of minnelide prodrug was initiated using an intravenous drug product, IND-enabling toxicology studies were conducted in both rats and dogs using the intravenous route of administration. The results of these studies supported first-in-human clinical trials involving intravenous administration of minnelide prodrug to patients with advanced solid tumors. To support the clinical development of a new solid oral dosage form of minnelide prodrug (capsules), exploratory and definitive toxicity studies were conducted with minnelide prodrug in solution via oral gavage in dogs. Taken together, the results of the intravenous and oral toxicity studies conducted with minnelide prodrug indicate that the target organ profile of minnelide prodrug is consistent in both species (rats and dogs) when administered by either route of administration (intravenous or oral). In each definitive toxicity study conducted with minnelide prodrug, adverse, largely irreversible histopathological effects were noted in reproductive tract tissues of both males and females. Additional effects on primary and/or secondary lymphoid tissues were noted in some studies. No adverse histopathological effects were noted on the gastrointestinal tract of dogs administered minnelide prodrug via oral gavage for up to 28 consecutive days.

While oral minnelide prodrug is easier to administer than intravenous formulations, it continues to have toxicities at high doses (thus, a dose limiting toxicity (DLT)) and side effects at high dose levels. Accordingly, there is a need for safer ways to administer minnelide prodrug and a need for other drug combination therapies with minnelide prodrug that enhance the effectiveness of the combination therapy, while limiting the toxicity of individual drugs used in the therapy. Furthermore, despite the availability of known antitumor agents, there continues to be a need for novel treatment regimens that are more effective and better tolerated by patients.

SUMMARY

Minnelide™ prodrug was determined to have potent antitumor activity against pancreatic and ovarian tumor cells in vitro (when "activated" with alkaline phosphatase to release triptolide) and markedly improved animal survival and significantly reduced tumor volumes and weights when administered daily in models of pancreatic and ovarian cancer.

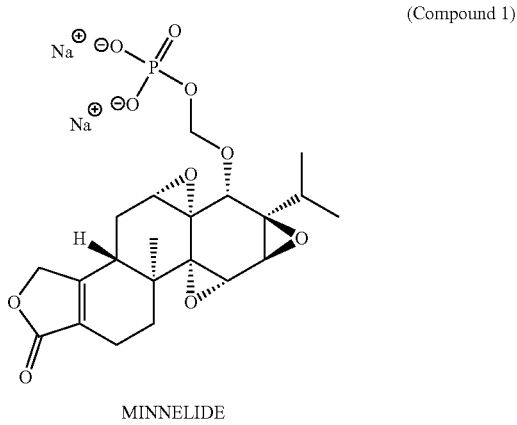

(Compound 1)

MINNELIDE

Gastric cancer is the most prevalent cancer in South Korea and worldwide. Minnelide prodrug has shown effectiveness in various cancers, including gastric cancer, in several pre-clinical models and in human trials in the United States. Minnelide prodrug in combination with paclitaxel has shown significant antitumor activity in pre-clinical models of pancreatic cancers and in ongoing US clinical trial in pancreatic and breast cancers. Herein, we have evaluated efficacy of minnelide prodrug in combination with paclitaxel in a subcutaneous mouse model of gastric cancer and in a human clinical trial. The results indicate that minnelide prodrug and paclitaxel alone or in combination have no significant toxic effects when properly dosed, and treating mice with a combination of low doses of minnelide prodrug and paclitaxel results in a significant decrease in tumor burden as compared to minnelide prodrug or paclitaxel alone. Further analysis of the tumors showed that the combination therapy was not only successful in reducing tumor growth, but also promotes tumor shrinkage in the animal models used in the study. The study therefore demonstrates that a combination of minnelide prodrug and paclitaxel, properly dosed, is an effective therapy for gastric cancer.

Accordingly, this disclosure provides a method for treating gastric cancer in a cancer patient, the method comprising administering to the cancer patient during a 28 day cycle a therapeutically effective combination of:
 a) about 0.25 mg to about 2.0 mg of minnelide prodrug according to a first regimen wherein a dose is given once per day on days 1 to 5, 8 to 12, and 15 to 19 of the cycle; and
 b) about 60 mg/m$^2$ to about 100 mg/m$^2$ of paclitaxel according to a second regimen wherein a dose is given once per day on days 1, 8, and 15 of the cycle;

wherein the 28-day cycle is repeated one or more times, and the combination effectively treats the gastric cancer.

The described technology provides for the use of the compositions described herein for use in medical therapy. The medical therapy can be treating cancer, for example, gastric cancer, breast cancer, colon cancer, lung cancer, pancreatic cancer, or prostate cancer. The invention also provides for the use of a composition as described herein for the manufacture of a medicament to treat a disease in a mammal, for example, cancer in a human. The medicament can include a pharmaceutically acceptable diluent, excipient, or carrier.

BRIEF DESCRIPTION OF THE DRAWINGS

The following drawings form part of the specification and are included to further demonstrate certain embodiments or various aspects of the invention. In some instances, embodiments of the invention can be best understood by referring to the accompanying drawings in combination with the detailed description presented herein. The description and accompanying drawings may highlight a certain specific example, or a certain aspect of the invention. However, one skilled in the art will understand that portions of the example or aspect may be used in combination with other examples or aspects of the invention.

DETAILED DESCRIPTION

Figure 1:
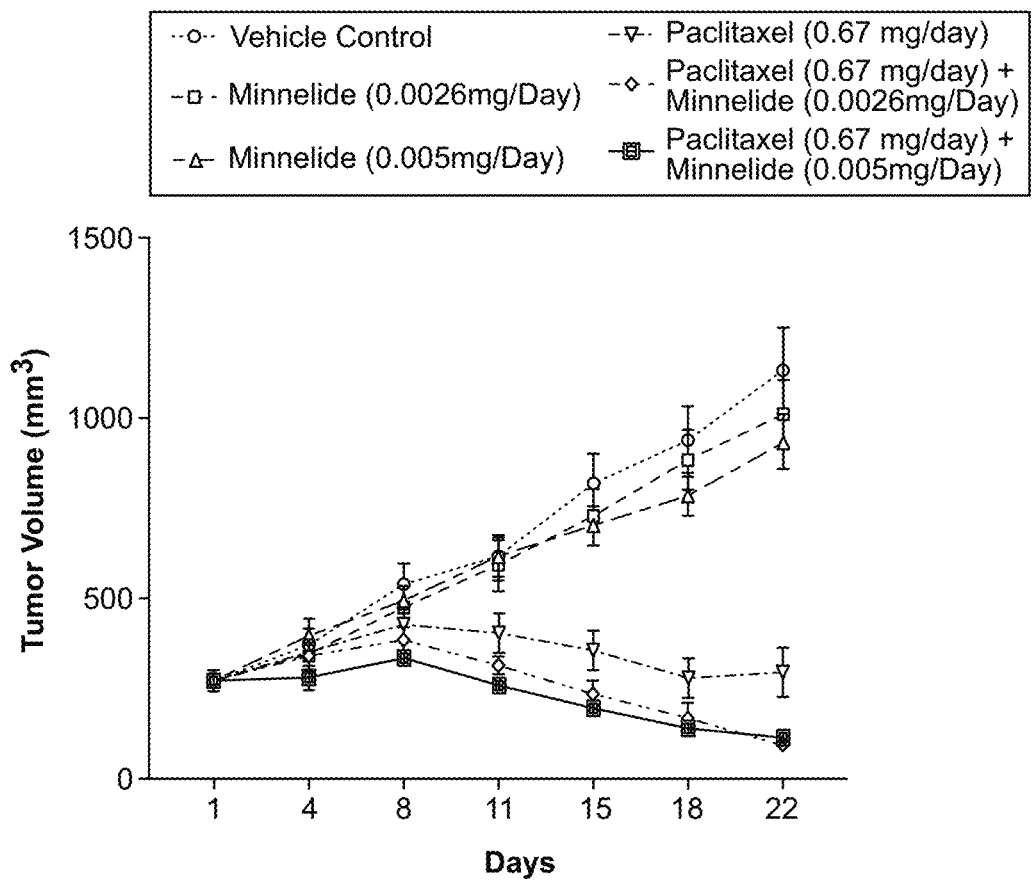
FIG. 1. Tumor progression in mice treated with minnelide prodrug or in combination with paclitaxel.
Figure 2A:
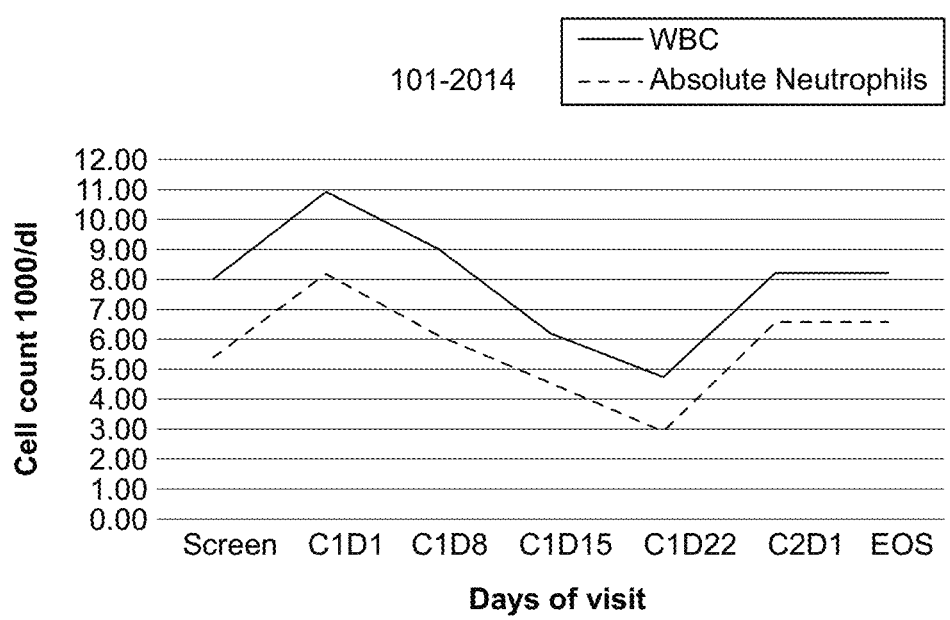
FIG. 2A-I. Regimen B: Graphs showing cell count (1000/dl) vs. dosing cycle/day of visit for subject id number. (A-D) Paclitaxel 60 mg/m$^2$ plus minnelide prodrug 0.25 mg/day for 21 days. (E-I) Paclitaxel 80 mg/m$^2$ plus minnelide prodrug 0.25 mg/day for 21 days.
Figure 2B:
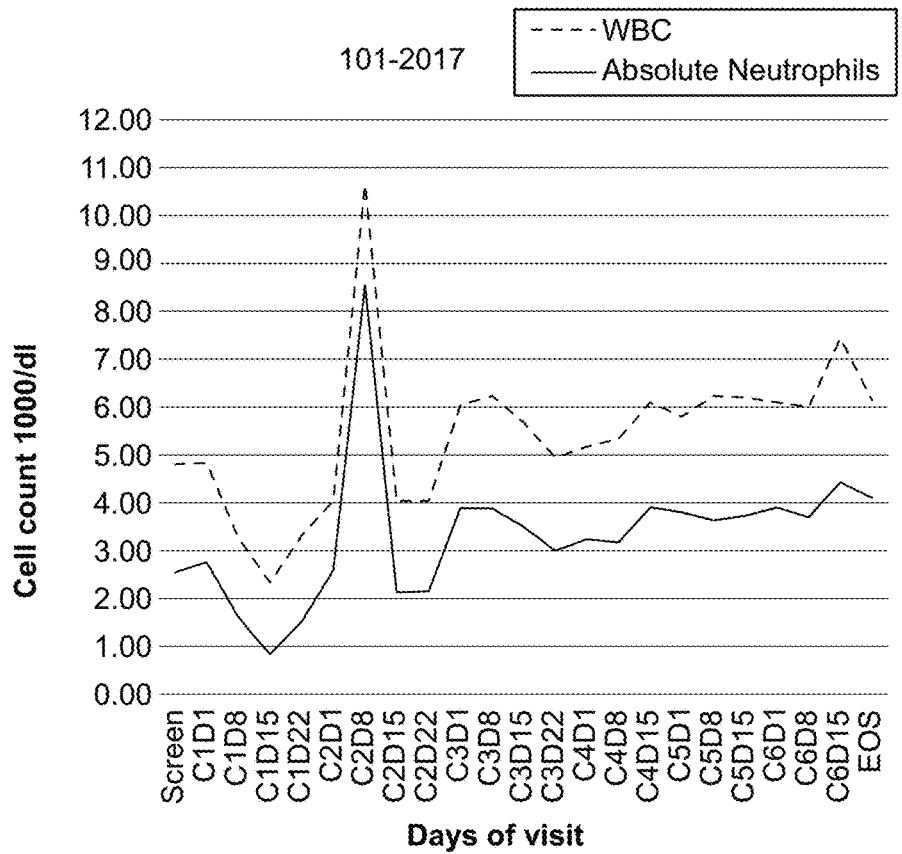
Figure 2C:
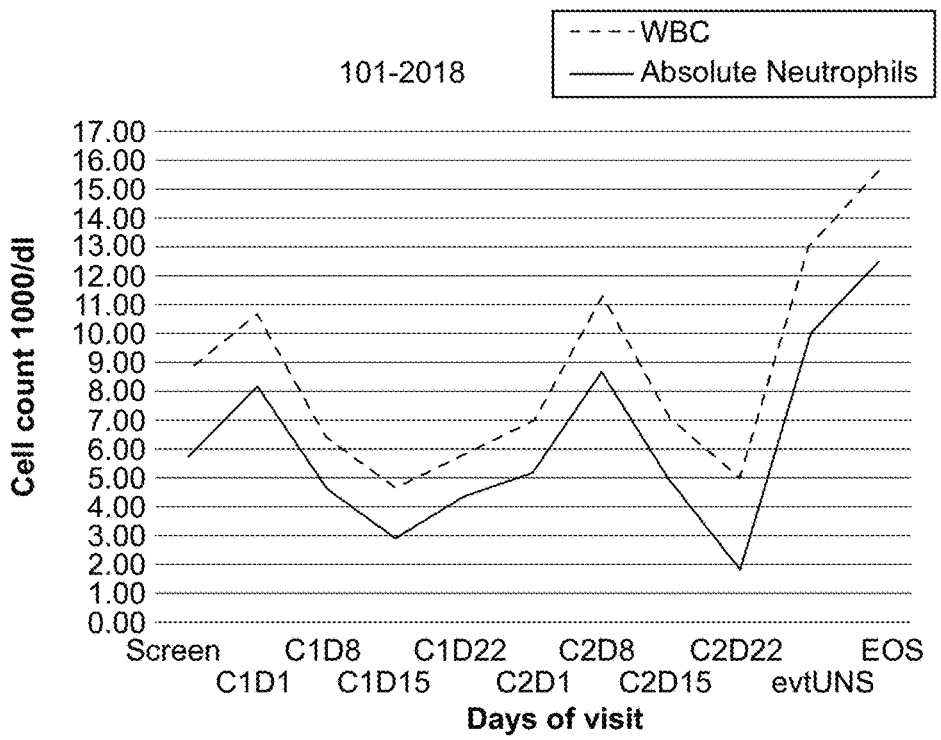
Figure 2D:
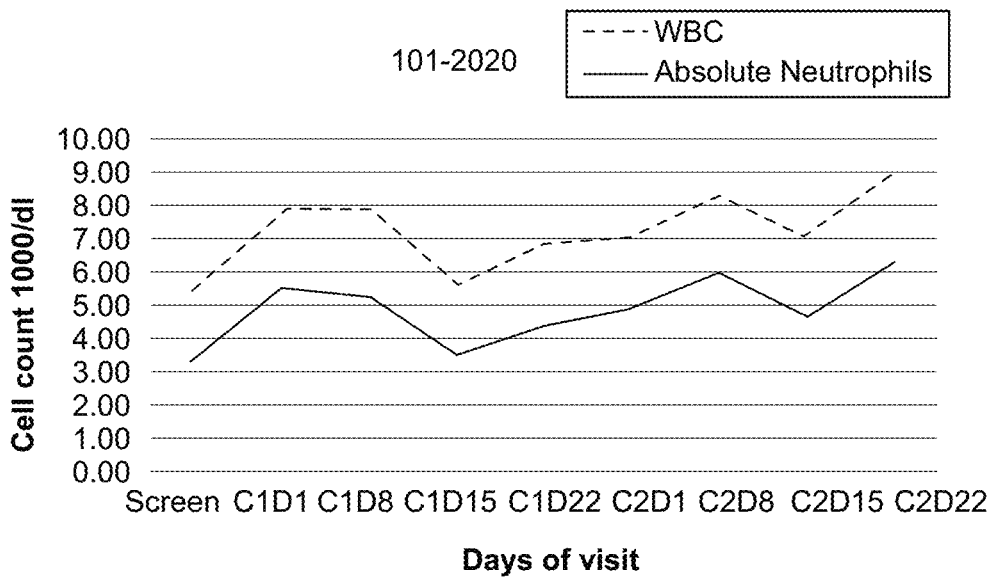
Figure 2E:
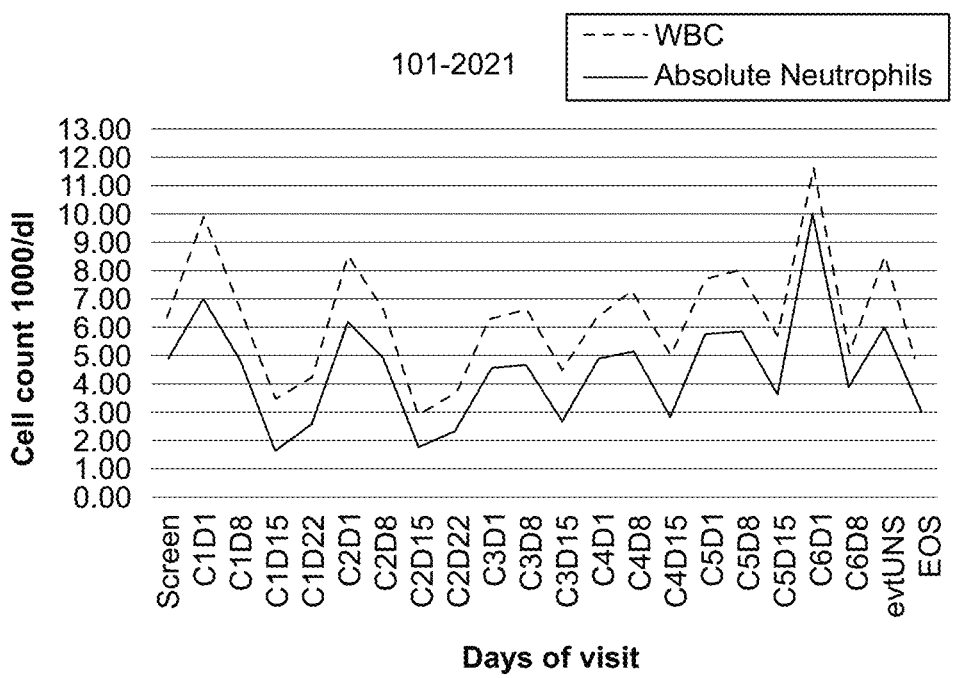
Figure 2F:
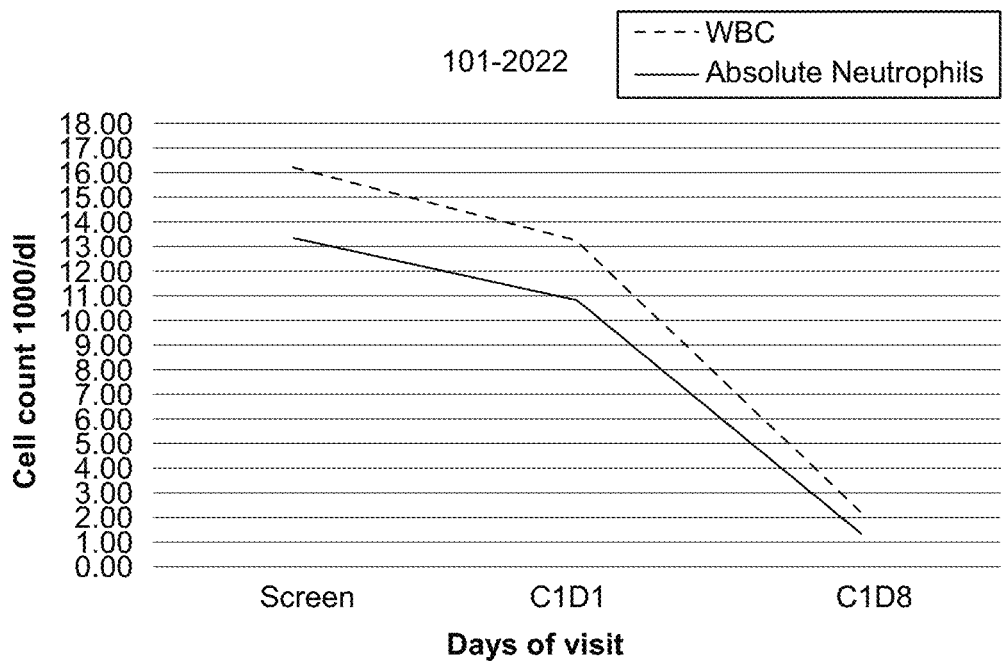
Figure 2G:
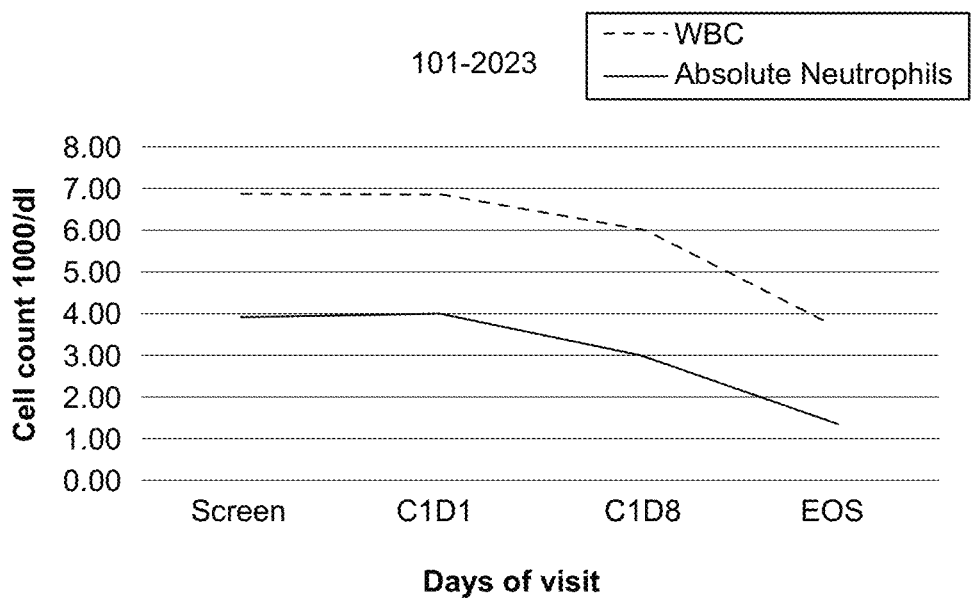
Figure 2H:
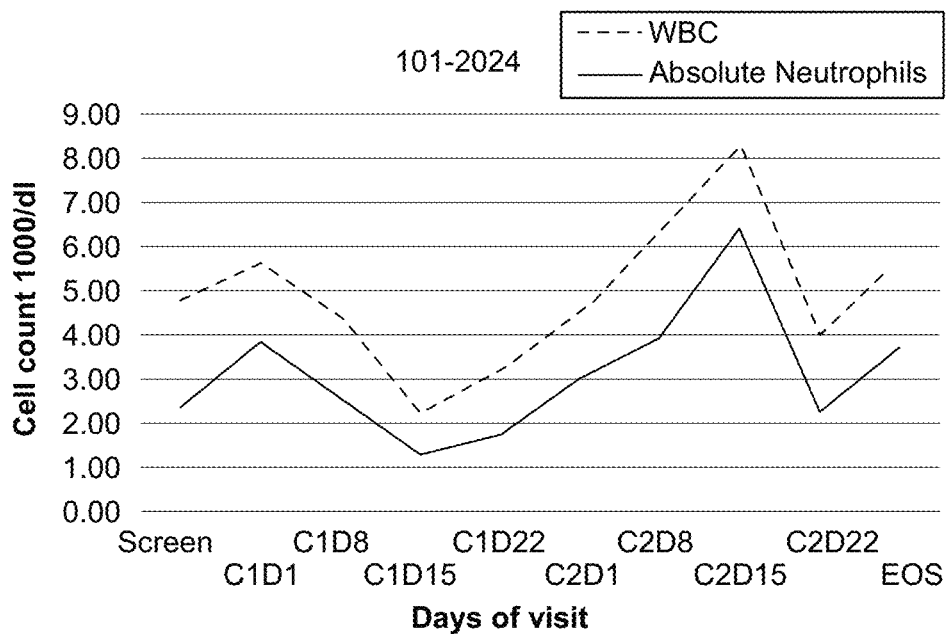
Figure 2I:
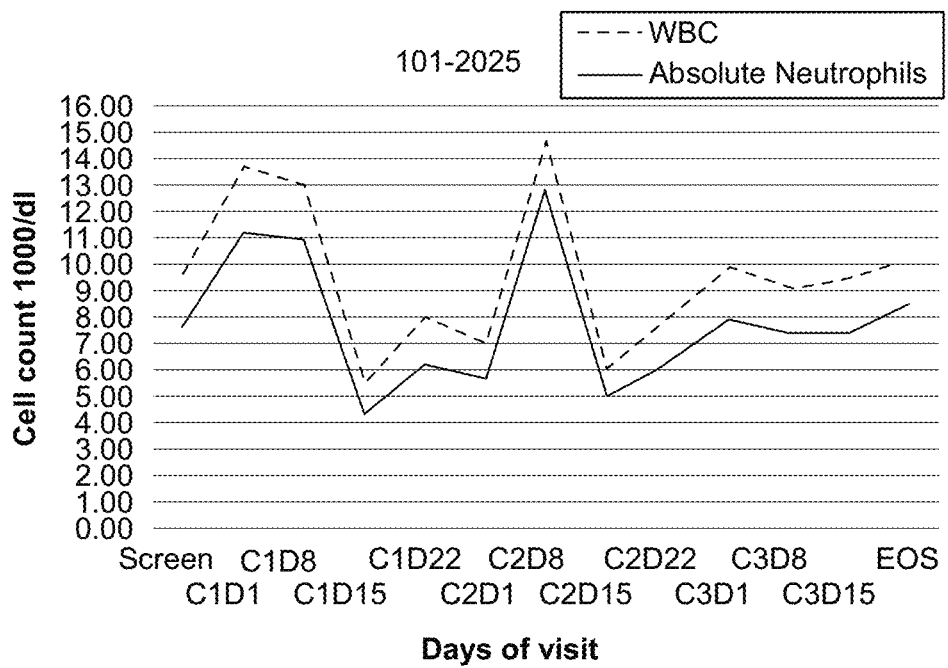
Figure 3A:
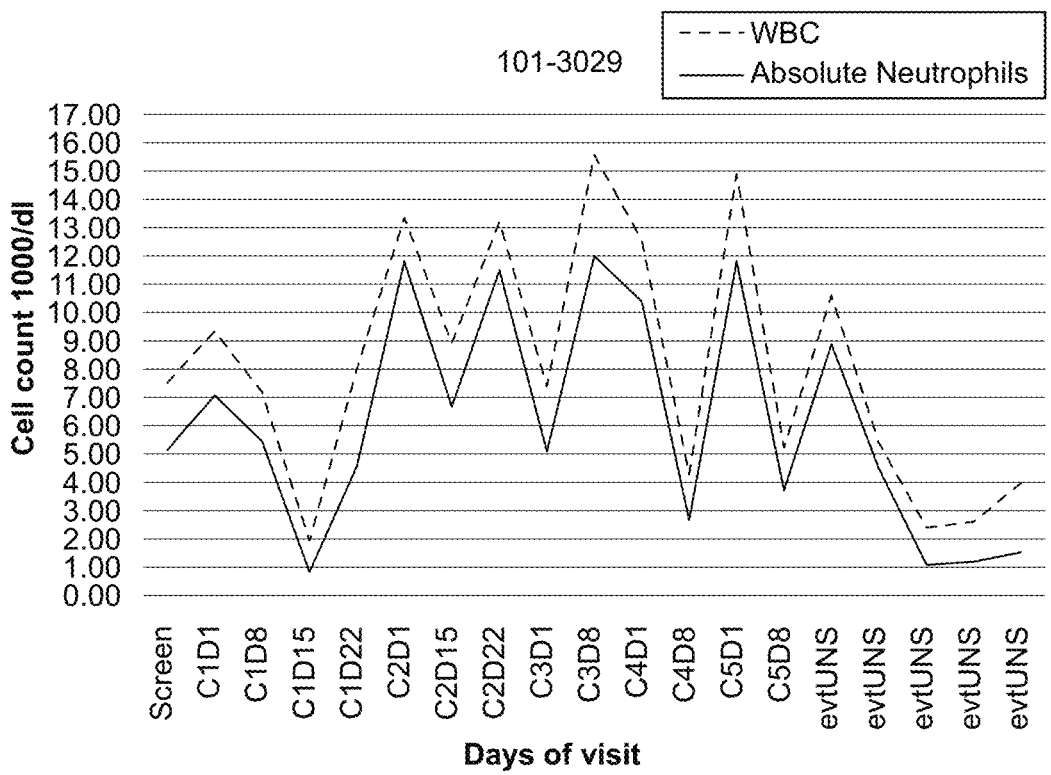
FIG. 3A-G. Regimen C: Graphs showing cell count (1000/dl) vs. dosing cycle/day for subject id number. (A-C) Paclitaxel 80 mg/m$^2$ plus minnelide prodrug 0.50 mg/day on 1-5 days, 9-12 days, and 12 to 15 days. (D-G) Paclitaxel 80 mg/m$^2$ plus minnelide prodrug 0.75 mg/day on 1-5 days, 9-12 days, and 12 to 15 days.
Figure 3B:
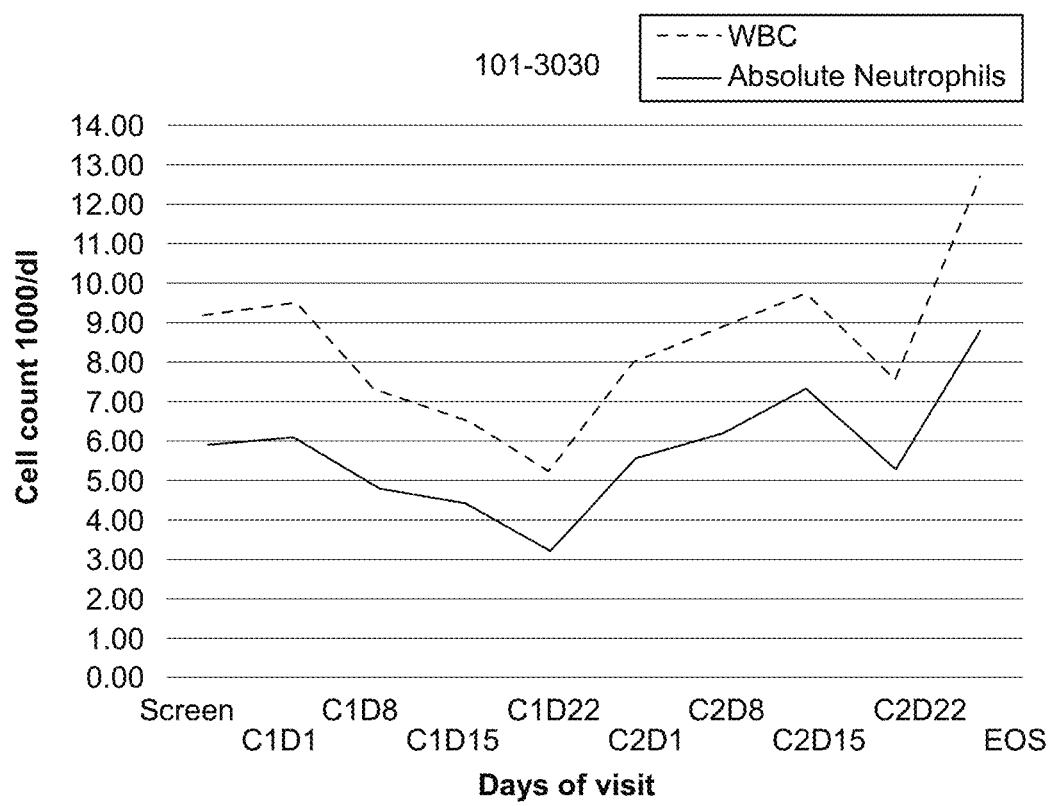
Figure 3C:
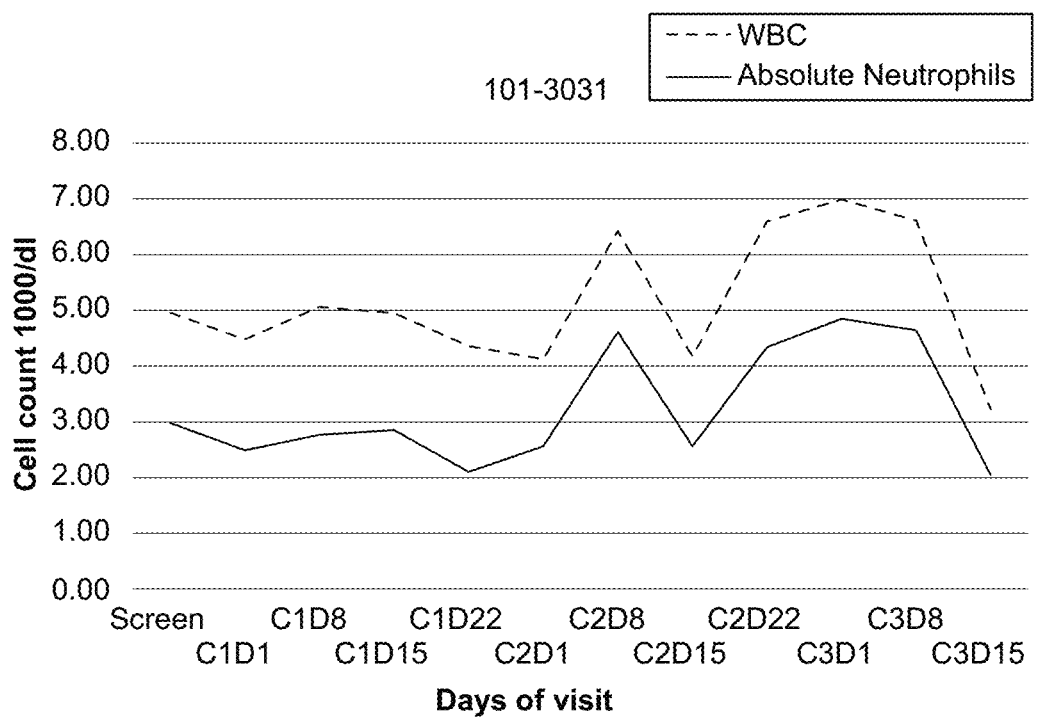
Figure 3D:
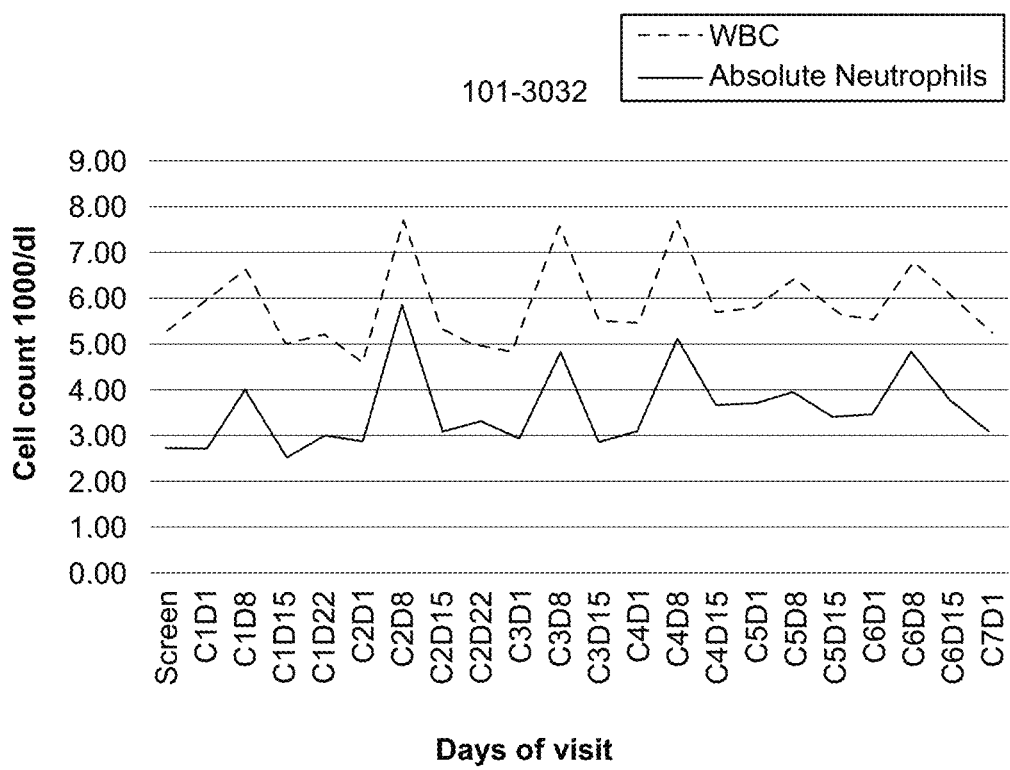
Figure 3E:
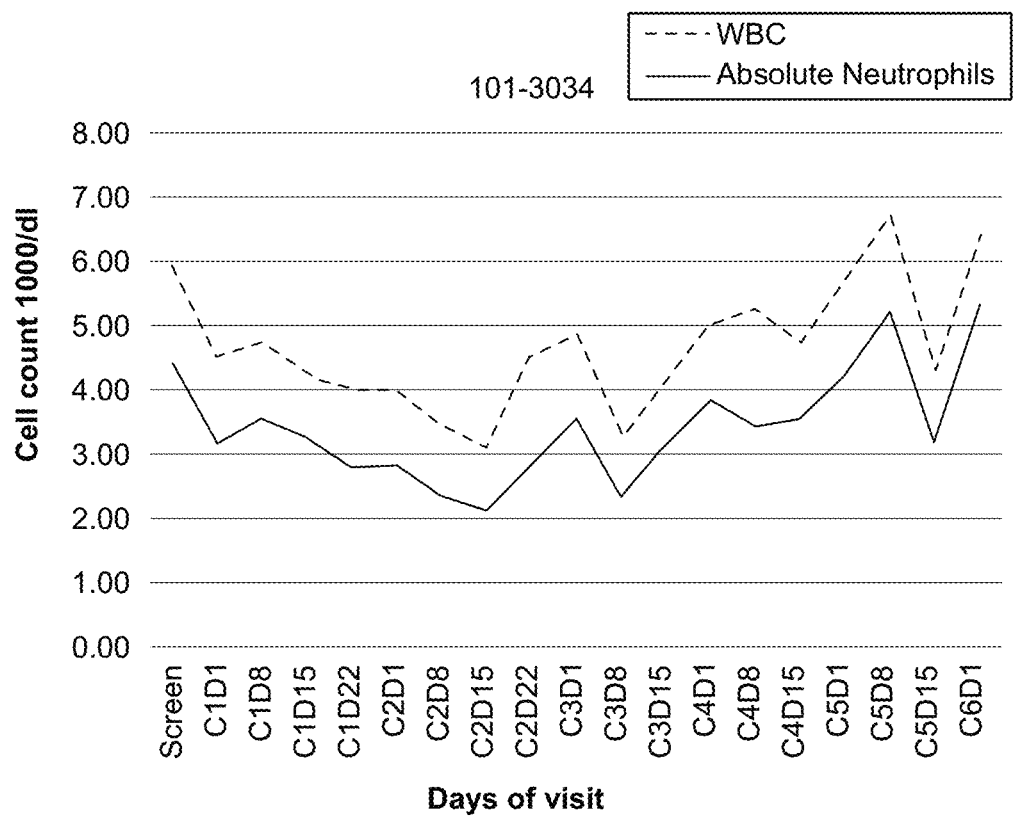
Figure 3F:
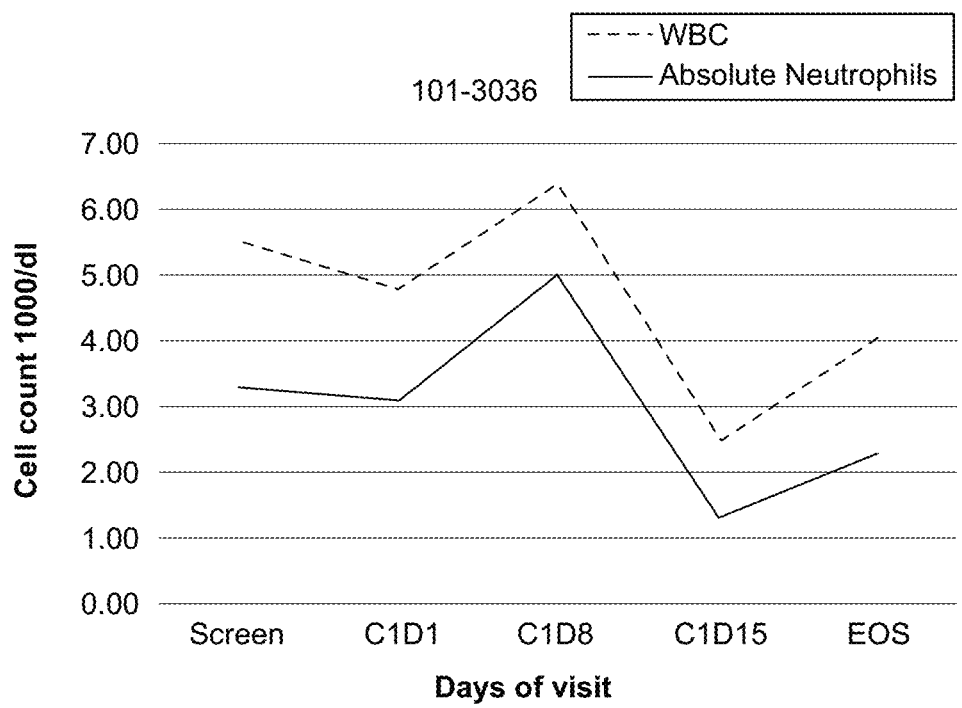
Figure 3G:
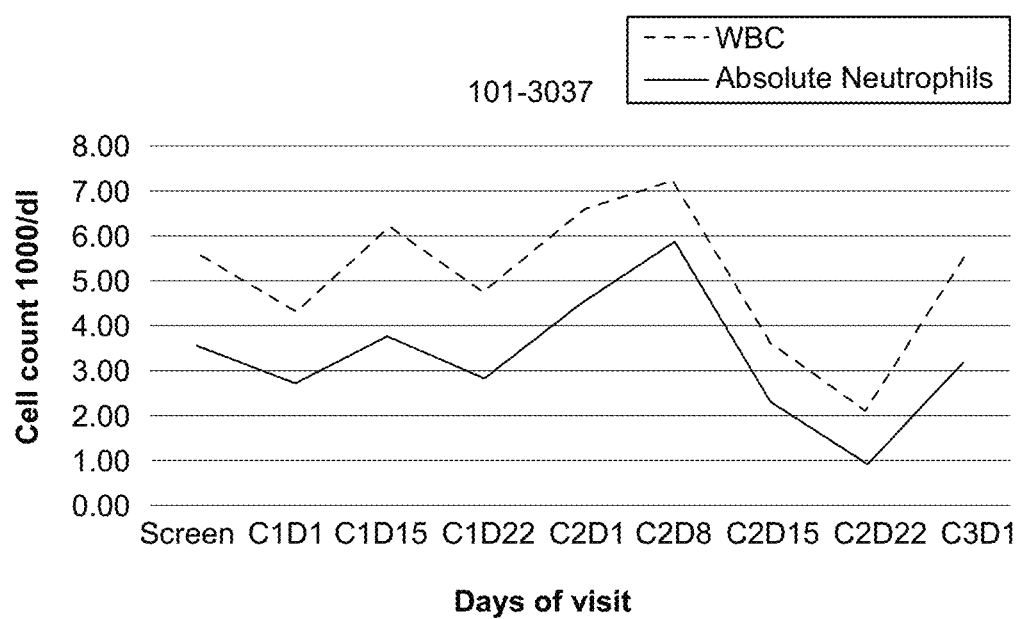

The results of the current studies indicate that combination therapy of low dose minnelide prodrug and paclitaxel (standard of care dose of the drug) was unexpectedly synergistic in reducing the tumor growth as compared to the single agent in the mouse model of gastric cancer (FIG. 1). Further analysis of the tumors showed that the combination therapy was not only successful in reducing tumor growth but also promotes tumor shrinkage in the animal models used in the study. Therefore, these studies show that a combination of minnelide prodrug and paclitaxel is an effective therapy for cancers, particularly gastric cancer.

Additional information and data supporting the invention can be found in U.S. Pat. No. 8,507,552 (Georg) and U.S. Pat. No. 9,150,600 (Georg), which patents are incorporated herein by reference.

Definitions

The following definitions are included to provide a clear and consistent understanding of the specification and claims. As used herein, the recited terms have the following meanings. All other terms and phrases used in this specification have their ordinary meanings as one of skill in the art would understand. Such ordinary meanings may be obtained by reference to technical dictionaries, such as *Hawley's Condensed Chemical Dictionary* 14$^{th}$ Edition, by R. J. Lewis, John Wiley & Sons, New York, N.Y., 2001.

References in the specification to "one embodiment", "an embodiment", etc., indicate that the embodiment described may include a particular aspect, feature, structure, moiety, or characteristic, but not every embodiment necessarily includes that aspect, feature, structure, moiety, or characteristic. Moreover, such phrases may, but do not necessarily, refer to the same embodiment referred to in other portions of the specification. Further, when a particular aspect, feature, structure, moiety, or characteristic is described in connection with an embodiment, it is within the knowledge of one skilled in the art to affect or connect such aspect, feature, structure, moiety, or characteristic with other embodiments, whether or not explicitly described.

The singular forms "a," "an," and "the" include plural reference unless the context clearly dictates otherwise. Thus, for example, a reference to "a compound" includes a plurality of such compounds, so that a compound X includes a plurality of compounds X. It is further noted that the claims may be drafted to exclude any optional element. As such, this statement is intended to serve as antecedent basis for the use of exclusive terminology, such as "solely," "only," and the like, in connection with any element described herein, and/or the recitation of claim elements or use of "negative" limitations.

The term "and/or" means any one of the items, any combination of the items, or all of the items with which this term is associated. The phrases "one or more" and "at least one" are readily understood by one of skill in the art, particularly when read in context of its usage. For example, the phrase can mean one, two, three, four, five, six, ten, 100, or any upper limit approximately 10, 100, or 1000 times higher than a recited lower limit. For example, one or more substituents on a phenyl ring refers to one to five, or one to four, for example if the phenyl ring is disubstituted.

As will be understood by the skilled artisan, all numbers, including those expressing quantities of ingredients, properties such as molecular weight, reaction conditions, and so forth, are approximations and are understood as being optionally modified in all instances by the term "about." These values can vary depending upon the desired properties sought to be obtained by those skilled in the art utilizing the teachings of the descriptions herein. It is also understood that such values inherently contain variability resulting from the standard deviations found in their respective testing measurements. When values are expressed as approximations, by use of the antecedent "about," it will be understood that the particular value without the modifier "about" also forms a further aspect.

The terms "about" and "approximately" are used interchangeably. Both terms can refer to a variation of ±5%, ±10%, ±20%, or ±25% of the value specified. For example, "about 50" percent can in some embodiments carry a variation from 45 to 55 percent, or as otherwise defined by a particular claim. For integer ranges, the term "about" can include one or two integers greater than and/or less than a recited integer at each end of the range. Unless indicated otherwise herein, the terms "about" and "approximately" are intended to include values, e.g., weight percentages, proximate to the recited range that are equivalent in terms of the functionality of the individual ingredient, composition, or embodiment. The terms "about" and "approximately" can also modify the endpoints of a recited range as discussed above in this paragraph.

As will be understood by one skilled in the art, for any and all purposes, particularly in terms of providing a written description, all ranges recited herein also encompass any and all possible sub-ranges and combinations of sub-ranges thereof, as well as the individual values making up the range, particularly integer values. It is therefore understood that each unit between two particular units are also disclosed. For example, if 10 to 15 is disclosed, then 11, 12, 13, and 14 are also disclosed, individually, and as part of a range. A recited range (e.g., weight percentages or carbon groups) includes each specific value, integer, decimal, or identity within the range. Any listed range can be easily recognized as sufficiently describing and enabling the same range being broken down into at least equal halves, thirds, quarters, fifths, or tenths. As a non-limiting example, each range discussed herein can be readily broken down into a lower third, middle third and upper third, etc. As will also be understood by one skilled in the art, all language such as "up to", "at least", "greater than", "less than", "more than", "or more", and the like, include the number recited and such terms refer to ranges that can be subsequently broken down into sub-ranges as discussed above. In the same manner, all ratios recited herein also include all sub-ratios falling within the broader ratio. Accordingly, specific values recited for radicals, substituents, and ranges, are for illustration only; they do not exclude other defined values or other values within defined ranges for radicals and substituents. It will be further understood that the endpoints of each of the ranges are significant both in relation to the other endpoint, and independently of the other endpoint.

This disclosure provides ranges, limits, and deviations to variables such as volume, mass, percentages, ratios, etc. It is understood by an ordinary person skilled in the art that a range, such as "number1" to "number2", implies a continuous range of numbers that includes the whole numbers and fractional numbers. For example, 1 to 10 means 1, 2, 3, 4, 5, . . . 9, 10. It also means 1.0, 1.1, 1.2, 1.3, . . . , 9.8, 9.9, 10.0, and also means 1.01, 1.02, 1.03, and so on. If the variable disclosed is a number less than "number10", it implies a continuous range that includes whole numbers and fractional numbers less than number10, as discussed above. Similarly, if the variable disclosed is a number greater than "number10", it implies a continuous range that includes whole numbers and fractional numbers greater than number10. These ranges can be modified by the term "about", whose meaning has been described above.

The recitation of a), b), c), . . . or i), ii), iii), or the like in a list of components or steps do not confer any particular order unless explicitly stated.

One skilled in the art will also readily recognize that where members are grouped together in a common manner, such as in a Markush group, the invention encompasses not only the entire group listed as a whole, but each member of the group individually and all possible subgroups of the main group. Additionally, for all purposes, the invention encompasses not only the main group, but also the main group absent one or more of the group members. The invention therefore envisages the explicit exclusion of any one or more of members of a recited group. Accordingly, provisos may apply to any of the disclosed categories or embodiments whereby any one or more of the recited elements, species, or embodiments, may be excluded from such categories or embodiments, for example, for use in an explicit negative limitation.

The term "contacting" refers to the act of touching, making contact, or of bringing to immediate or close proximity, including at the cellular or molecular level, for example, to bring about a physiological reaction, a chemical reaction, or a physical change, e.g., in a solution, in a reaction mixture, in vitro, or in vivo.

An "effective amount" refers to an amount effective to treat a disease, disorder, and/or condition, or to bring about a recited effect. For example, an effective amount can be an amount effective to reduce the progression or severity of the condition or symptoms being treated. Determination of a therapeutically effective amount is well within the capacity of persons skilled in the art. The term "effective amount" is intended to include an amount of a compound described herein, or an amount of a combination of compounds described herein, e.g., that is effective to treat or prevent a disease or disorder, or to treat the symptoms of the disease or disorder, in a host. Thus, an "effective amount" generally means an amount that provides the desired effect.

Alternatively, the terms "effective amount" or "therapeutically effective amount," as used herein, refer to a sufficient amount of an agent or a composition or combination of compositions being administered which will relieve to some extent one or more of the symptoms of the disease or condition being treated. The result can be reduction and/or alleviation of the signs, symptoms, or causes of a disease, or any other desired alteration of a biological system. For example, an "effective amount" for therapeutic uses is the amount of the composition comprising a compound as disclosed herein required to provide a clinically significant decrease in disease symptoms. An appropriate "effective" amount in any individual case may be determined using techniques, such as a dose escalation study. The dose could be administered in one or more administrations. However, the precise determination of what would be considered an effective dose may be based on factors individual to each patient, including, but not limited to, the patient's age, size, type or extent of disease, stage of the disease, route of administration of the compositions, the type or extent of supplemental therapy used, ongoing disease process and type of treatment desired (e.g., aggressive vs. conventional treatment).

The terms "treating", "treat" and "treatment" include (i) preventing a disease, pathologic or medical condition from occurring (e.g., prophylaxis); (ii) inhibiting the disease, pathologic or medical condition or arresting its development; (iii) relieving the disease, pathologic or medical condition; and/or (iv) diminishing symptoms associated with the disease, pathologic or medical condition. Thus, the terms "treat", "treatment", and "treating" can extend to prophylaxis and can include prevent, prevention, preventing, lowering, stopping or reversing the progression or severity of the condition or symptoms being treated. As such, the term "treatment" can include medical, therapeutic, and/or prophylactic administration, as appropriate.

As used herein, "subject" or "patient" means an individual having symptoms of, or at risk for, a disease or other malignancy. A patient may be human or non-human and may include, for example, animal strains or species used as "model systems" for research purposes, such a mouse model as described herein. Likewise, the patient may include either adults or juveniles (e.g., children). Moreover, patient may mean any living organism, preferably a mammal (e.g., human or non-human) that may benefit from the administration of compositions contemplated herein. Examples of mammals include, but are not limited to, any member of the Mammalian class: humans, non-human primates such as chimpanzees, and other apes and monkey species; farm animals such as cattle, horses, sheep, goats, swine; domestic animals such as rabbits, dogs, and cats; laboratory animals including rodents, such as rats, mice and guinea pigs, and the like. Examples of non-mammals include, but are not limited to, birds, fish and the like. In one embodiment of the methods provided herein, the mammal is a human.

As used herein, the terms "providing", "administering", "introducing", are used interchangeably herein and refer to the placement of a compound of the disclosure into a subject by a method or route that results in at least partial localization of the compound to a desired site. The compound can be administered by any appropriate route that results in delivery to a desired location in the subject.

The compound and compositions described herein may be administered with additional compositions to prolong stability and activity of the compositions, or in combination with other therapeutic drugs.

The terms "inhibit", "inhibiting", and "inhibition" refer to the slowing, halting, or reversing the growth or progression of a disease, infection, condition, or group of cells. The inhibition can be greater than about 20%, 40%, 60%, 80%, 90%, 95%, or 99%, for example, compared to the growth or progression that occurs in the absence of the treatment or contacting.

The term "substantially" as used herein, is a broad term and is used in its ordinary sense, including, without limitation, being largely but not necessarily wholly that which is specified. For example, the term could refer to a numerical value that may not be 100% the full numerical value. The full numerical value may be less by about 1%, about 2%, about 3%, about 4%, about 5%, about 6%, about 7%, about 8%, about 9%, about 10%, about 15%, or about 20%.

Wherever the term "comprising" is used herein, options are contemplated wherein the terms "consisting of" or "consisting essentially of" are used instead. As used herein, "comprising" is synonymous with "including," "containing". or "characterized by", and is inclusive or open-ended and does not exclude additional, unrecited elements or method steps. As used herein, "consisting of" excludes any element, step, or ingredient not specified in the aspect element. As used herein, "consisting essentially of" does not exclude materials or steps that do not materially affect the basic and novel characteristics of the aspect. In each instance herein any of the terms "comprising", "consisting essentially of" and "consisting of" may be replaced with either of the other two terms. The disclosure illustratively described herein may be suitably practiced in the absence of any element or elements, limitation or limitations which is not specifically disclosed herein.

The term "adverse event" refers to any untoward medical occurrence associated with the use of a drug in humans, whether or not considered drug related.

The term "serious adverse event" refers to death, a life-threatening adverse event, inpatient hospitalization or prolongation of existing hospitalization, a persistent or significant incapacity or substantial disruption of the ability to conduct normal life functions, or a congenital anomaly/birth defect. Important medical events that may not result in death, be life-threatening, or require hospitalization may be considered serious when, such medical events include allergic bronchospasm requiring intensive treatment in an emergency room or at home, blood dyscrasias or convulsions that do not result in inpatient hospitalization, or the development of drug dependency or drug abuse, etc.

The term "regimen" refers to a course of medical treatment over a period of time. The regimen described herein includes one or more sub-regimens, such as a first regimen, a second regime, and so on, that make up the entire regimen of medical treatment. The period of time for treatment may be one or more days, one or more weeks, one or more months, etc., wherein the period of time may be repeated in a cyclic fashion one or more times. For example, a period of time may be 28 days, defining the length of a cycle that may be repeated. A regimen may be a 28 day cycle where a compound A is administered on specific days of the cycle, defining a first regimen, and where compound B is administered on other specific days of the cycle that define a second regimen, which in total defines the entire regimen.

The minnelide prodrug (MINNELIDE, or Minnelide™ prodrug) is also known as 14-O-phosphonooxymethyltriptolide disodium salt, the IUPAC chemical name for which is: disodium; [(1S,2S,4S,5S,7S,8R,9R,11S, 13S)-1-methyl-17-oxo-7-propan-2-yl-3,6,10,16-tetraoxaheptacyclo [11.7.0.0$^{2,4}$.0$^{2,9}$.0$^{5,7}$.0$^{9,11}$.0$^{14,18}$]icos-14 (18)-en-8-yl]oxymethyl phosphate. The neutral compound and pharmaceutically acceptable salt forms thereof are referred to herein as the minnelide prodrug or compound 1.

Embodiments of the Technology.

This disclosure provides a method for treating cancer in a cancer patient, the method comprising administering to a gastric cancer patient during a 28 day cycle a therapeutically effective combination of:
  a) about 0.25 mg to about 2.0 mg of minnelide prodrug according to a first regimen wherein a dose is given once per day on days 1 to 5, 8 to 12, and 15 to 19 of the cycle; and
  b) about 60 mg/m$^2$ to about 100 mg/m$^2$ of paclitaxel according to a second regimen wherein a dose is given once per day on days 1, 8, and 15 of the cycle;
  wherein the 28-day cycle is repeated one or more times and the combination effectively treats the cancer.

In various embodiments, the cancer patient is administered about 0.25 mg to about 1.25 mg of minnelide prodrug according to the first regimen. In various embodiments, according to the first regimen, the cancer patient is administered a milligram amount of minnelide prodrug that is about 0.15 mg, 0.25 mg, 0.35 mg, 0.4 mg, 0.5 mg, 0.6 mg, 0.7 mg, 0.8 mg, 0.9 mg, 1.0 mg, 1.1 mg, 1.2 mg, 1.3 mg, 1.4 mg, 1.5 mg, 1.6 mg, 1.7 mg, 1.8 mg, 1.9 mg, 2.0 mg, 2.2 mg, 2.3 mg, 2.4 mg, 2.5 mg, 2.6 mg, 2.7 mg, 2.8 mg, 2.9 mg, 3.0 mg, 3.5 mg, 4.0 mg, 4.5 mg, 5.0 mg, 5.5 mg, or about 6.0 mg.

In various embodiments, the cancer patient is administered about 50 mg/m$^2$ to about 100 mg/m$^2$ of paclitaxel according to the second regimen. In various embodiments, according to the second regimen, the cancer patient is administered a milligram of paclitaxel that is about 5 mg/m$^2$, 10 mg/m$^2$, 15 mg/m$^2$, 20 mg/m$^2$, 25 mg/m$^2$, 30 mg/m$^2$, 35 mg/m$^2$, 40 mg/m$^2$, 45 mg/m$^2$, 50 mg/m$^2$, 55 mg/m$^2$, 60 mg/m$^2$, 65 mg/m$^2$, 70 mg/m$^2$, 75 mg/m$^2$, 80 mg/m$^2$, 85 mg/m$^2$, 90 mg/m$^2$, 95 mg/m$^2$, 100 mg/m$^2$, 125 mg/m$^2$, 150 mg/m$^2$, 175 mg/m$^2$, or about 200 mg/m$^2$.

In some embodiments, the cancer patient is administered about 0.25 mg of minnelide according to the first regimen and about 60 mg/m$^2$ of paclitaxel according to the second regimen.

In some embodiments, the cancer patient is administered about 0.25 mg of minnelide according to the first regimen and about 80 mg/m$^2$ of paclitaxel according to the second regimen.

In some embodiments, the cancer patient is administered about 0.5 mg of minnelide according to the first regimen and about 80 mg/m$^2$ of paclitaxel according to the second regimen.

In some embodiments, the cancer patient is administered about 0.75 mg of minnelide according to the first regimen and about 80 mg/m$^2$ of paclitaxel according to the second regimen.

In some embodiments, the cancer patient is administered about 1 mg of minnelide according to the first regimen and about 80 mg/m$^2$ of paclitaxel according to the second regimen.

In some embodiments, the cancer patient is administered about 1.25 mg of minnelide according to the first regimen and about 80 mg/m$^2$ of paclitaxel according to the second regimen.

In some embodiments, the cancer patient is administered about 1.5 mg of minnelide according to the first regimen and about 80 mg/m$^2$ of paclitaxel according to the second regimen.

In some embodiments, the cancer patient is administered about 1.75 mg of minnelide according to the first regimen and about 80 mg/m$^2$ of paclitaxel according to the second regimen.

In some embodiments, the cancer patient is administered about 2 mg of minnelide according to the first regimen and about 80 mg/m$^2$ of paclitaxel according to the second regimen.

In various embodiments, minnelide prodrug is administered orally or intravenously, preferably orally. In various embodiments, paclitaxel is administered intravenously or orally, preferably intravenously.

In various embodiments, the cancer patient also has one or more of pancreatic cancer, ovarian cancer, liver cancer, lung cancer, breast cancer, bladder cancer, and skin cancer. In some embodiments, the cancer patient has been diagnosed with advanced gastric cancer (AGC). The method can effectively treat a cancer patient suffering from or further suffering from gastric cancer and one or more of pancreatic cancer, ovarian cancer, liver cancer, lung cancer, breast cancer, bladder cancer, and skin cancer.

In various embodiments, the cancer patient is a human. In various embodiments, the cancer patient is a female human or a male human. In other embodiments, the cancer patient is a juvenile female human or a juvenile male human.

In various embodiments, the combination effectively treats the cancer without causing a complete blood count of the cancer patient to lower by more than 25%, 20%, 15%, 10%, or 5% from baseline. In various embodiments, the combination effectively treats the cancer without causing a platelet count or an absolute neutrophil count in the cancer patient to lower by more than 25%, 20%, 15%, 10%, or 5% from baseline.

In some embodiments, the cancer patient has tumors that continued to progress after receiving paclitaxel chemotherapy, and in various embodiments described herein, the tumors of the cancer patient are reduced in diameter by 30% or greater after two, three, four, or five or more 28-day cycles.

In some embodiments, the methods described herein are used to treat a cancer that has become refractory, or to treat a cancer that is resistant or non-responsive to other methods of cancer treatment. In various embodiments, the cancer is gastric cancer, for example, advanced gastric cancer (AGC).

In one specific embodiment, the invention provides a method for treating advanced gastric cancer in a cancer patient that has tumors that continued to progress after receiving paclitaxel chemotherapy, the method comprising administering to a cancer patient diagnosed with advanced gastric cancer during a 28 day cycle a therapeutically effective combination of:
  a) about 0.5 mg to about 1.5 mg of minnelide administered orally according to a first regimen wherein a dose is given once per day on days 1 to 5, 8 to 12, and 15 to 19 of the cycle; and b) about 70 mg/m$^2$ to about 90 mg/m$^2$ of paclitaxel administered intravenously according to a second regimen wherein a dose is given once per day on days 1, 8, and 15 of the cycle;
  wherein the 28-day cycle is repeated two or more times, thereby achieving disease stability or disease regression of the advanced gastric cancer. In various embodiments, the combination effectively treats the gastric cancer without causing a complete blood count of the cancer patient to lower by more than 25% from baseline, and the combination effectively treats the gastric cancer without causing a platelet count or an absolute neutrophil count in the cancer patient to lower by more than 25% from baseline.

Classification of Adverse Events by Severity.

The severity of each Adverse Event (AE) follows guidelines from the National Cancer Institute Common Terminology Criteria for Adverse Events (NCI CTCAE), which are summarized as follows.

Grade 1: An AE that is transient or mild discomfort, not interfering with the patient's daily activity performance or functioning; medical intervention/therapy may be required.

Grade 2: An AE of sufficient severity as to possibly make the patient moderately uncomfortable; possibly influencing the patient's daily activity performance or functioning; generally, not impairing the patient's ability to continue in the study; and/or possibly needing therapeutic intervention.

Grade 3: An AE event generally causing severe discomfort, significantly influencing the patient's daily activity performance or functioning, generally requiring alteration or cessation of study drug administration, and/or generally requiring therapeutic intervention with hospitalization possible.

Grade 4: An AE that is considered to be life threatening, resulting in significant disability or incapacity, and/or representing the worst possible occurrence of that event with hospitalization probable Grade 5: A death related to an AE. .

Clinical Experience.

Intravenous Minnelide Prodrug. Phase 1, Multi-Center, Open-Label, Dose-Escalation, Safety, Pharmacokinetic, and Pharmacodynamic Study of minnelide prodrug given intravenously daily for 21 days followed by 7 days off schedule in patients with Advanced Gastrointestinal Tumors. A second dosing schedule of minnelide prodrug given intravenously QD for 5 days with 2 days off for three weeks followed by a 7-day rest period was also explored during this study.

A total of 45 patients enrolled in the Phase 1 study, however 3 patients were not dosed with study drug. The remaining 42 patients were dosed in the study. The primary reason for the discontinuation of treatment was disease progression. There were 6 deaths in the study, but these occurred after the study drug had ended and were within the 30-day follow-up period. The deaths that occurred during the study were found to be not related to the study drug and were found to be related to progression of the patient's disease (pancreatic/gastric cancer). One patient who died from respiratory failure, and this was also found to be not related to use of the study drug.

There were 3 patients who discontinued the study drug due to a treatment emergent adverse events (TEAEs). All instances were considered Grade 3, and two of these TEAEs were considered as likely related to use of the study drug. These two cases were also considered DLTs. A total of 28 Serious Adverse Events occurred in 17 patients and six were found to be related to the study drug.

The most commonly reported TEAE (>20%) regardless of causality included: hypoalbuminemia, anemia, hypoproteinemia, fatigue, neutropenia, leukopenia, thrombocytopenia, nausea, hypocalcemia, diarrhea, hyperphosphatemia, constipation, vomiting, hyponatremia, lymphopenia, abdominal pain, dehydration, hyperglycemia, peripheral edema, hypophosphatemia, and headache.

A total of 32 patients had at least 1 adverse event (AE) that was considered related to the study drug. Adverse events of neutropenia grade 3 and 4 of short durations have been observed at all dose levels and were determined to be drug related. The neutropenia resolved within a couple of days of not receiving treatment. Neutropenic fever and neutropenic infection were observed in three patients and determined to be drug related. Anemia and thrombocytopenia Grade 3 and 4 were observed in 22% of the patients and determined to be drug related. Other side effects of any grade that were possibly related to the drug included nausea, vomiting, diarrhea, constipation, anorexia, stomatitis, cerebellar toxicity, embolism and dyspnea, which occurred in ≤3% of the patients.

Oral Minnelide Prodrug. A Phase 1, Multi-Center, Open-Label, Dose-Escalation, Safety, Pharmacokinetic, and Pharmacodynamic Study of Minnelide™ Capsules given alone or in combination with protein-bound paclitaxel in patients with Advanced Solid Tumors. A total of 44 patients were enrolled and dosed in the Phase 1 study, 32 in the monotherapy regimen, and 12 in the combination regimen. The primary reason for discontinuation of treatment has been disease progression. There were 9 deaths in the study, 7 of which were assessed as not related to minnelide prodrug and were after discontinuation of the study drug. One patient on the 1.25 mg monotherapy regimen passed away from G5 related sepsis. One patient on the combination regimen at 0.25 mg of minnelide prodrug passed away from G5 sepsis, which after investigation and review of pharmacokinetic data, was found to be unrelated to minnelide prodrug.

Four patients discontinued the study drug due to a treatment-emergent adverse event (TEAE). Two instances were considered Grade 5, one was Grade 3, one was Grade 2. One of the TEAEs was considered likely related to use of the study drug, the other three possibly related (two Grade 5 sepsis, one Grade 3 hypokalemia, one Grade 2 neutrophil count decrease). Three SAE cases were considered dose limiting toxicities (DLTs). These events included: two events of sepsis and one case of influenza A pneumonia. A total of 28 Serious Adverse Events occurred in 17 patients and 4 were found to be related to the study drug.

Adverse Events classified according to responses noted with Minnelide Prodrug 0.25 mg plus either protein bound paclitaxel 80 mg m$^2$ or 100 mg m$^2$ dose. The most commonly reported TEAE (>20%) regardless of causality included: Anemia, Abdominal Pain, Constipation, Vomiting, Diarrhea, Nausea, Fatigue, Hypokalemia, and Hypoalbuminaemia. Twenty-seven patients had at least 1 AE that was considered related to the study drug. The Grade 3 to Grade 5 TEAEs reported for minnelide prodrug 0.25 mg plus either protein bound paclitaxel 80 mg/m$^2$ or 100 mg/m$^2$ dose were as follows:

Grade 3 Adverse Events: Cellulitis 2%, Hypokalemia 9%, Hypotension 2%, Hypophosphatemia 2%, Leukopenia 2%, Nausea 2%, Neutropenia 25%, Sepsis 2%, Thrombocytopenia 2%, Vomiting 2%, Weight decreased 2%.

Grade 4 Adverse Events: *Aeromonas* infection 2%, Lactic Acidosis 2%, Leukopenia 2%, Lymphocytopenia 2%, Multiple organ dysfunction syndrome 2%, Neutropenia 9%, Grade 5 Adverse Event: Sepsis 5%. During our minnelide prodrug plus protein bound paclitaxel regimen, we treated 10 patients with either pancreatic or breast cancer. Two patients showed partial response, 6 patients had stable disease, one patient had progressive disease, and one patient had dose limiting toxicity.

Dose Escalation Studies.

The objective of the dose escalation was to define the safety and toxicity characteristics (e.g., the maximum tolerated dose (MTD) and the dose limiting toxicities (DLT)) of Minnelide™ Capsules as monotherapy in advanced gastric cancer (Regimen A) and in combination with paclitaxel in gastric cancers (Regimen B and C).

Regimen A (monotherapy). Minnelide™ Capsules were given as a single agent orally once daily×21 days followed by a 7-day rest period. One cycle was 28 days. Minnelide™ Capsules were given with the patient in a fasting state.

Regimen B (combination). Minnelide™ Capsules were given orally once daily×21 days in combination with paclitaxel given intravenously on days 1, 8 and 15. One cycle was 28 days. Minnelide™ Capsules were given with the patient in a fasting state.

Regimen ((combination). Minnelide™ Capsules was given orally once daily on days 1 to 5, 8 to 12 and 15 to 19 in combination with paclitaxel given intravenously on days 1, 8 and 15. One cycle was 28 days. Minnelide™ Capsules were given with the patient in a fasting state.

Dose-Limiting Toxicity. Dose-limiting toxicities (DLT) were evaluated during Cycle 1 of treatment. Toxicities were graded and documented according to the NCI CTCAE guidelines (described above). Dose reductions were not allowed during Cycle 1. DLTs include adverse events that are considered to be related to the study drug, including:

Grade 4 neutropenia lasting ≥5 days, Grade 4 neutropenia with use of growth factor, or Grade 3 or 4 neutropenia with fever and/or infection;

Grade 4 thrombocytopenia (or Grade 3 with bleeding);

Grade 3 or 4 treatment-related non-hematological toxicity (Grade 3 nausea, vomiting or diarrhea that last >72 hours despite maximal treatment constitutes a DLT; or a dosing delay of greater than 2 weeks due to a treatment-emergent AE or related severe laboratory abnormality.

Inclusion Criteria for Study Eligibility.

Patients meeting study participation eligibility signed IRB-approved informed consent and met the following inclusion criteria.

1. Patients with histologically confirmed advanced gastric cancer (AGC).
2. Tumor progression after receiving standard/approved chemotherapy or where there is no approved therapy.
3. One or more metastatic tumors measurable per RECIST v1.1 Criteria.
4. Karnofsky performance 70% (cares for self but unable to carry on normal activity).
5. Life expectancy of at least 3 months.
6. Age ≥19 years.
7. A negative pregnancy test (if female).
8. Acceptable liver function: Bilirubin≤1.5 times upper limit of normal (ULN); Aspartate aminotransferase (AST), serum glutamic oxaloacetic transaminase (SGOT), alanine aminotransferase (ALT), serum glutamic pyruvic transaminase (SGPT), and Alkaline phosphatase≤2.5 times upper limit of normal (if liver metastases are present, then ≤5×ULN is allowed); Albumin ≥3.0 g/dL.
9. Acceptable renal function: Serum creatinine within normal limits, OR calculated creatinine clearance ≥60 mL/min/1.73 m$^2$ for patients with creatinine levels above institutional normal.
10. Acceptable hematologic status: Absolute neutrophil count for Monotherapy: ≥1,500 cells/mm$^3$, or Combination therapy with paclitaxel: ≥2,000 cells/mm$^3$; Platelet count ≥100,000 (plt/mm$^3$); Hemoglobin ≥9 g/dL.
11. Urinalysis: No clinically significant abnormalities.
12. Acceptable coagulation status: Prothrombin time (PT) ≤1.5 times institutional ULN; Partial thromboplastin time (PTT)≤1.5 times institutional ULN.
13. Women of child-bearing potential and men must agree to use adequate contraception for men and women of child-producing potential, the use of effective contraceptive methods during the study and until 90 days after the last dose of IP for men or until 6 months after the last dose of IP for women or 6 months after the last dose of IP with paclitaxel for both men and women.

Dose Interruptions for Minnelide Prodrug.

A drop in blood counts is usually seen within the first 5-7 days of the start of minnelide prodrug and resolved in 4-8 days of withholding the drug.

CBC with differential was done on days 1, 8, 15, 22 and more frequently as clinically indicated. Patient were hospitalized for close monitoring when the ANC level was <1000 mm$^3$ (grade 3 or higher) or platelet was <100,000 cells/mm$^3$ at any time. Minnelide™ Capsules would not resume until the ANC level was ≥1500 mm$^3$ or platelet was ≥100,000 cells/mm$^3$.

The following Examples are intended to illustrate the above invention and should not be construed as to narrow its scope. One skilled in the art will readily recognize that the Examples suggest many other ways in which the invention could be practiced. It should be understood that numerous variations and modifications may be made while remaining within the scope of the invention.

EXAMPLES

Example 1. Gastric Cancer Therapy Regimen a (Monotherapy)

Minnelide™ Capsules were given as a single agent orally once daily×21 days followed by a 7-day rest period. Dose escalation for Regimen A was followed according to Table 1. At each dose level the first patient was treated. If the patient did not develop CTCAE V4.03 Grade 3 or greater toxicity after one week of treatment, a second patient and a third patient could receive the same dose of Minnelide™ Capsules (capsules containing minnelide prodrug). If the second and third patients do not experience CTCAE V4.03 Grade 3 or greater toxicity after a minimum of three weeks of treatment, dose escalation will proceed to dose level 2.

If a DLT is observed in 1 out of 3 patients at the first dose level, up to an additional 3 patients will be enrolled and treated at that dose level. If two patients at this dose level have DLTs, dosing will be decreased to ½ of dose level 1. If 1 of 6 patients has a DLT, the dose will be increased to the second dose level. If 2 or more of the up to 6 patients at the second dose level have DLTs, the preceding dose (dose level 1) will be declared the MTD. If 1 or less of 6 patients has a DLT, the dose level 2 will be declared the MTD.

TABLE 1

Dose Escalation Dosing Regimen A (monotherapy).
Dose Escalation
Dosing regimen A (monotherapy)

| Dose Level | % Increments from prior dose level | Dose |
|---|---|---|
| 1 | — | 1.0 mg/day |
| 2 | 25% | 1.25 mg/day |
| 3 | 20% | 1.50 mg/day |
| 4 | 17% | 1.75 mg |
| 5 | 14% | 2.0 mg |

Example 2. Gastric Cancer Therapy Regimen B (Combination)

Minnelide™ Capsules were given orally once daily×21 days in combination with paclitaxel given intravenously on days 1, 8 and 15. Once dose level 1 in Regimen A (monotherapy) had been cleared, dose escalation in Regimen B (combination) was begun following Table 2. At each dose level the first patient was treated. If the patient did not develop CTCAE V4.03 Grade 3 or greater toxicity after one week of treatment, a second patient and a third patient could receive the same dose of Minnelide™ Capsules and paclitaxel. Paclitaxel is given at 60 mg/m² as a starting dose and increased to 80 mg/m² if no DLTs were noted in 3 patients and would remain at 80 mg/m², and dose levels for the escalation of the minnelide prodrug would proceed as outlined in Table 2. Escalation would proceed according to the parameters described for Regimen A.

TABLE 2

Dose Escalation Dosing Regimen B (see FIG. 2).
Dose Escalation [a]
Dosing regimen B (combination)

| Dose Level | Dose Level Minnelide™ Capsules | paclitaxel on days 1, 8, 15 | Number of Patients |
|---|---|---|---|
| 1 | 0.25 mg | 60 mg/m² | 3 + 3 |
| 2 | 0.25 mg | 80 mg/m² | 3 + 3 |
| 3 | 0.50 mg | 80 mg/m² | 3 + 3 |
| 4 | 0.75 mg | 80 mg/m² | 3 + 3 |
| 5 | 1.0 mg | 80 mg/m² | 3 + 3 |
| 6 | 1.25 mg | 80 mg/m² | 3 + 3 |

[a] Additional dose levels beyond dose level 6 could proceed with minnelide prodrug 0.25 mg increments when supported by safety data.

Example 3. Gastric Cancer Therapy Regimen C (Combination)

Minnelide™ Capsules were given orally once daily on days 1 to 5, 8 to 12 and 15 to 19 in combination with paclitaxel given intravenously on days 1, 8 and 15. Dose escalation in Regimen C (combination) would begin following Table 3. At each dose level the first patient was treated. If the patient did not develop CTCAE V4.03 Grade 3 or greater toxicity after one week of treatment, a second patient and a third patient would receive the same dose of Minnelide™ Capsules and paclitaxel. Paclitaxel was given at 80 mg/m² if no DLTs were noted in 3 patients and would remain at 80 mg/m², and dose levels for the escalation of the minnelide prodrug would proceed as outlined in Table 3. Adjustments to the paclitaxel would be considered in Cycle 2 and beyond after a safety evaluation.

TABLE 3

Dose Escalation Dosing Regimen C (see FIG. 3).
Dose Escalation [a]
Dosing regimen C (combination)

| Dose Level | Dose Level Minnelide™ Capsules | paclitaxel on days 1, 8, 15 | Number of Patients |
|---|---|---|---|
| 1 | 0.25 mg | 80 mg/m² | 3 + 3 |
| 2 | 0.50 mg | 80 mg/m² | 3 + 3 |
| 3 | 0.75 mg | 80 mg/m² | 3 + 3 |
| 4 | 1.0 mg | 80 mg/m² | 3 + 3 |
| 5 | 1.25 mg | 80 mg/m² | 3 + 3 |

[a] Additional dose levels beyond dose level 6 could proceed with minnelide prodrug 0.25 mg increments when supported by safety data.

Example 4. Disease Assessment (See Table 4 Below)

Target Lesions. Response criteria for target lesions are shown in Table 5. All measurable lesions up to a maximum of two lesions per organ and five lesions in total, representative of all involved organs, were identified as target lesions and recorded and measured at baseline. Target lesions were selected on the basis of their size (lesions with the longest diameter) and were representative of all involved organs, as well as their suitability for reproducible repeated measurements. All measurements were recorded using calipers if clinically assessed.

A sum of the diameters (longest for non-nodal lesions, short axis for nodal lesions) for all target lesions were calculated and reported as the baseline sum diameters, which were used as a reference to further characterize any objective tumor regression in the measurable dimension of the disease. If lymph nodes were included in the sum, only the short axis contributed.

therapy with minnelide prodrug (Regimen A) and Combination therapy (minnelide prodrug plus paclitaxel), which was further divided into Regimen B and C.

TABLE 4

Clinical evaluation of disease.
Minnelide 101 GC Regimen B and C (Minnelide plus Paclitaxel)

| Patient ID* | Gender/Age | Height in cm | Weight in kg | Body surface area m$^2$ | Minnelide Daily dose | Dose mg/m$^2$ | Evaluable Yes/No | No. of cycles completed | Imaging Response |
|---|---|---|---|---|---|---|---|---|---|
| Paclitaxel 60 mg/m$^2$ + Minnelide 0.25 mg/day cohort Regimen B | | | | | | | | | |
| 101-2014 | M/62 | 163.50 | 55.60 | 1.59 | 0.25 | 0.16 | Y | 1 | PD |
| 101-2017 | M/56 | 174.40 | 64.20 | 1.76 | 0.25 | 0.14 | N | 6 | SD |
| 101-2018 | M/66 | 173.50 | 53.60 | 1.61 | 0.25 | 0.16 | Y | 2 | PD |
| 101-2020 | M/69 | 169.20 | 59.80 | 1.68 | 0.25 | 0.15 | Y | 2 | PD |
| Paclitaxel 80 mg/m$^2$ + Minnelide 0.25 mg/day cohort Regimen B | | | | | | | | | |
| 101-2021 | F/56 | 154.50 | 62.2 | 1.63 | 0.25 | 0.15 | Y | 6 | SD |
| 101-2022 | M/65 | 169.80 | 55.7 | 1.62 | 0.25 | 0.15 | N | 1 | Withdrew |
| 101-2023 | M/62 | 177.50 | 53.3 | 1.62 | 0.25 | 0.15 | N | 0 | Withdrew |
| 101-2024 | F/33 | 161.90 | 53.6 | 1.55 | 0.25 | 0.16 | N | 2 | PD |
| 101-2025 | M/71 | 174.60 | 63.8 | 1.76 | 0.25 | 0.14 | Y | 2 | SD |
| 101-2026 | M/49 | 170.70 | 72.2 | 1.85 | 0.25 | 0.14 | Y | 1 | PD |
| Paclitaxel 80 mg/m$^2$ + Minnelide 0.50 mg/day cohort Regimen C | | | | | | | | | |
| 101-3029 | F/74 | 143.20 | 37.6 | 1.22 | 0.5 | 0.41 | Y | 5 | PR |
| 101-3030 | M/54 | 164.10 | 53.1 | 1.56 | 0.5 | 0.32 | Y | 2 | PD |
| 101-3031 | F/38 | 160.40 | 42.0 | 1.37 | 0.5 | 0.37 | Y | 3 | SD |
| Paclitaxel 80 mg/m$^2$ + Minnelide 0.75 mg/day cohort Regimen C | | | | | | | | | |
| 101-3032 | F/51 | 161.00 | 48.2 | 1.47 | 0.75 | 0.51 | Y | 6 | PR |
| 101-3034 | F/50 | 161.00 | 52.3 | 1.53 | 0.75 | 0.49 | Y | 6 | PR |
| 101-3036 | M/71 | 156.50 | 49.1 | 1.46 | 0.75 | 0.51 | N | 0 | Withdrew |
| 101-3037 | M/63 | 171.20 | 60.4 | 1.69 | 0.75 | 0.44 | Y | 2 | |
| Paclitaxel 80 mg/m$^2$ + Minnelide 1.0 mg/day cohort Regimen C | | | | | | | | | |
| 101-3038 | M/61 | 166.80 | 53.5 | 1.57 | 1.0 | 0.64 | Y | 1 | |
| 101-3040 | M/55 | 167.00 | 64.8 | 1.73 | 1.0 | 0.58 | | | |

*101-2017. IP dosing less than 17 due to ANC level-not evaluable.
*101-2022. Subject withdrew the consent and did not complete the 17 doses of IP for to be evaluable.
*101-2023. Subject withdrew due to feeling burdened by the frequent visit schedule and didn't complete the 17 doses of IP to be evaluable.
*101-2024. IP dosing less than 17 due to ANC level-not evaluable.
*101-3036. Subject withdrew due to feeling burdened by the frequent visit schedule and didn't complete the 17 doses of IP to be evaluable.

TABLE 5

Criteria for target lesions.

| | |
|---|---|
| Complete Response (CR) | Disappearance of all target lesions. Any pathological lymph nodes (whether target or non-target) must have reduction in short axis to <10 mm. |
| Partial Response (PR) | At least a 30% decrease in the sum of the diameters of target lesions, taking as reference the baseline sum of diameters |
| Progressive Disease (PD) | At least a 20% increase in the sum of the LD of target lesions, taking as reference the smallest sum on study (this may include the baseline sum). The sum must also demonstrate an absolute increase of at least 5 mm |
| Stable Disease (SD) | Neither sufficient shrinkage to qualify for PR nor sufficient increase to qualify for PD |

28-Day Dosing Regimens A-C.

| | |
|---|---|
| Regimen A | Minnelide Prodrug Monotherapy<br>Minnelide prodrug (PO) at 1 mg, escalating to 1.25 mg and 1.5 mg.<br>Once daily for 21 days followed by a 7-day rest period. |
| Regimen B | Minnelide Prodrug and Paclitaxel Combination Therapy<br>Minnelide prodrug (PO) at 0.25 mg.<br>Once daily for 21 days followed by a 7-day rest period.<br>Paclitaxel (IV) 60 mg/m$^2$, escalating to 80 mg/m$^2$.<br>Paclitaxel on days 1, 8 and 15 (Q4W). |
| Regimen C | Minnelide Prodrug and Paclitaxel Combination Therapy<br>Minnelide prodrug (PO) at 0.25 mg, escalating to 0.75 mg, 1 mg, and 1.25 mg.<br>Once daily on days 1 to 5, 8 to 12, and 15 to 19.<br>Paclitaxel (IV) 80 mg/m$^2$<br>Paclitaxel on days 1, 8 and 15 (Q4W). |

Example 5. A First-In-Human Phase 1 Study

This study, evaluating the safety and preliminary antitumor activity of minnelide prodrug was administered alone or with paclitaxel in patients with advanced gastric cancer (AGC) (NCT 05566834).

Study design. This was an open-label, nonrandomized, phase 1 study conducted at Samsung Medical Center (SMC) in Korea. The study consisted of three regimens: Mono- Patients. Adult (≥20 years of age) Korean patients with histologically confirmed advanced-unresectable or metastatic gastric or gastro-esophageal junction adenocarcinoma, who had failed initial standard therapy or for whom no standard treatment was available, were eligible to participate in the study, regardless of HER2 status. Study treatment was discontinued if the patient experienced radiological progressive disease (PD) per Response Evaluation Criteria in Solid Tumors version 1.1 (RECIST v1.1) as assessed by the investigator, clinical progression as assessed by the investigator, or developed unacceptable toxicity.

Treatments. In Regimen A, 3-5 patients were treated at escalating doses of minnelide prodrug alone to determine the maximum tolerated dose (MTD). Minnelide prodrug was administered per oral (PO) once daily for 21 days followed by a 7-day rest period, starting at 1 mg, and escalating to 1.25 mg, and 1.5 mg. One cycle was equal to 28 days and minnelide prodrug was given with the patient in a fasting state. In Regimen B, the same dosing scheme was used for minnelide prodrug 0.25 mg PO in combination with paclitaxel intravenously on days 1, 8 and 15 (Q4W), starting at 60 mg/m$^2$, and escalating to 80 mg/m$^2$. In Regimen C, patients were treated with paclitaxel 80 mg/m$^2$ given intravenously on days 1, 8 and 15 (Q4W) in combination with minnelide prodrug PO once daily on days 1 to 5, 8 to 12 and 15 to 19, starting at 0.5 mg, escalating to 0.75 mg, 1.0 mg, and 1.25 mg. Dose-limiting toxicities (DLTs) were assessed during cycle 1. Treatment continued until disease progression, death, unacceptable toxicity, or patient or investigator decision to discontinue.

Outcomes. In this phase 1 study, the primary objective was to determine the maximum tolerated dose (MTD) and the dose limiting toxicities (DLT) of minnelide prodrug when given alone or in combination with paclitaxel and to establish recommended phase 2 dose (RP2D) of single-agent minnelide prodrug and in combination with paclitaxel every 4 weeks. Secondary objectives were to assess any evidence of antitumor activity of minnelide prodrug alone and in combination with paclitaxel by objective radiographic assessment. Antitumor activity was assessed by objective response rate (ORR). Disease control rate (DCR), duration of response (DOR), progression-free survival (PFS) and overall survival (OS) analysis were performed.

Assessment. Adverse events were graded using National Cancer Institute Common Terminology Criteria for Adverse Events (NCI CTCAE), version 4.03. Tumor assessments were performed after cycles 2, 4, 6, and 8, and every 4 cycles thereafter, or as indicated. Response was determined by investigators using RECIST criteria, version 1.1. The objective response rate (ORR) was determined in patients with measurable disease at baseline and defined as complete response or partial response, confirmed by repeat assessment after 4 or more weeks. The disease control rate (DCR) was defined as the proportion of patients achieving complete response, partial response, or stable disease.

Statistical methods. Safety analyses were performed for the safety-evaluable population, which comprised all patients who received any study drug. Safety was assessed through DLTs and AEs. Patients with missing baseline or no response assessments were classified as non-responders. ORR and DCR were reported with exact 95% confidence intervals (CIs). PFS, OS, and DOR were estimated using the Kaplan-Meier method with 95% CIs. Safety data were summarized descriptively. Data are presented separately for Regimen A (minnelide prodrug monotherapy), and Regimen B and C (minnelide prodrug plus paclitaxel). Data analysis was performed on Dec. 20, 2023, using Statistical Package for the Social Sciences for Windows (version 27.0; IBM Corp. Armonk, NY, USA).

Results.

Figure 4:
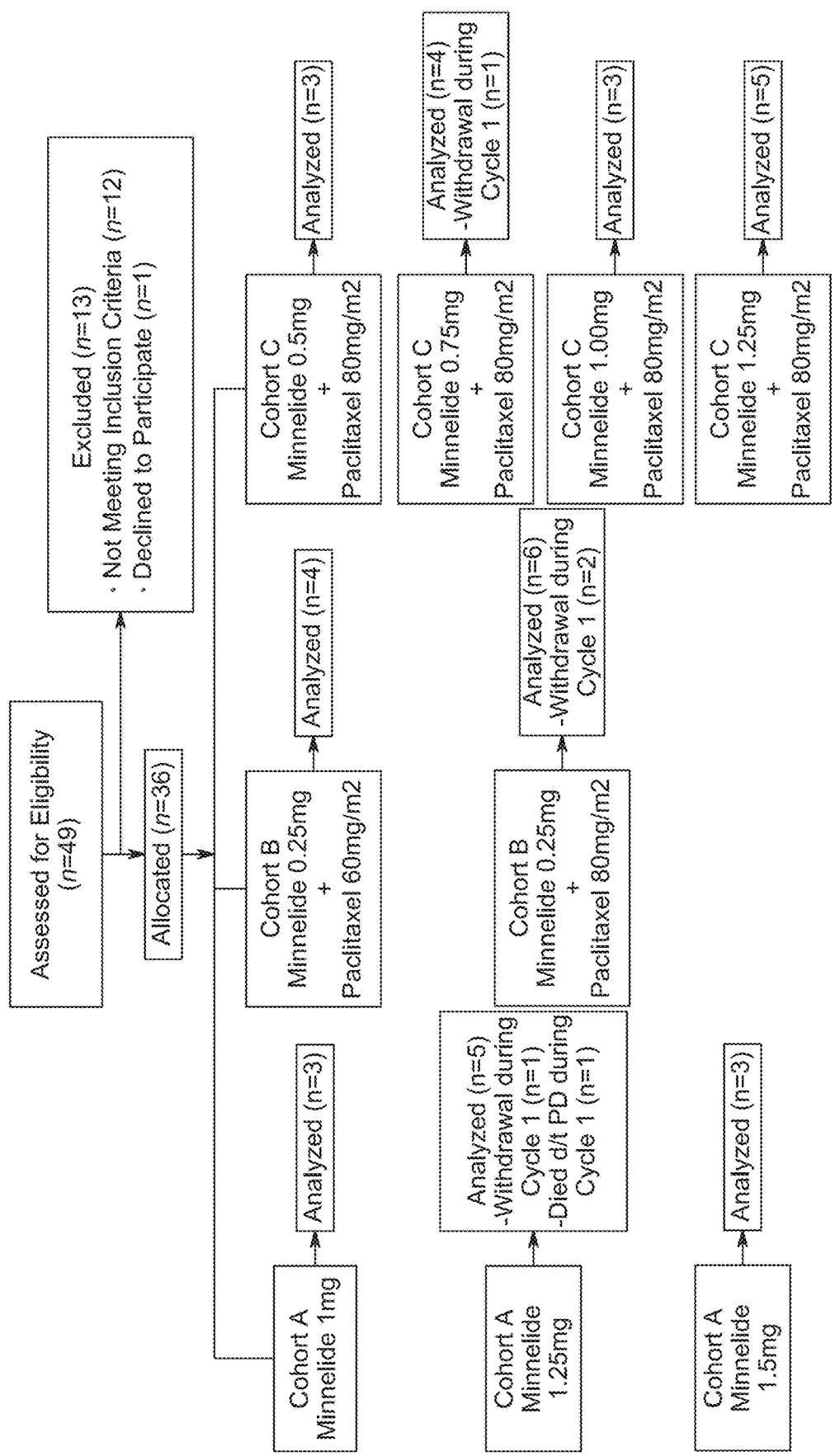
FIG. 4. Flowchart showing Example 5 patient disposition into cohort groups.

Patients. Between Nov. 2, 2020, and Oct. 18, 2023, 49 patients were screened and 36 patients (median age, 59 [range, 30-74]) met eligibility criteria and 11 were treated in Regimen A, 10 in Regimen B and 15 in Regimen C (FIG. 4 and Table 6). Study exclusions (n=13) were due to failing to meet inclusion criteria (n=12) or declining to participate in the study (n=1). All 36 enrolled patients were included in data analysis (FIG. 4). Baseline demographics and characteristics are summarized in Table 6.

The Regimen A comprised of 6 male and 5 female patients; all had an ECOG PS of 1 and had received median three prior cancer therapies (4 [36%] had received prior immunotherapy). The Regimen B comprised of 8 male and 2 female patients and received median three prior cancer therapies (3 [30%] had received prior immunotherapy). The Regimen C comprised of 8 male and 7 female patients and received median two prior therapies (range, 1-5) and 8 (53%) had received prior immunotherapy. In total, six (17%) patients had HER2-positive tumors and 19 (76%) had PD-L1 (CPS ≥1) expressed tumors (Table 6). None of the patients had microsatellite instability-high tumors. In the combination treatment group, 80% of patients in Regimen B and 53.3% of patients in Regimen C were previously treated with paclitaxel.

TABLE 6

Patient demographics and clinical characteristics.

| | Regimen A (Minnelide mono) (n = 11) No. (%) | Regimen B (Minnelide plus Paclitaxel combination) (n = 10) No. (%) | Regimen C (Minnelide plus Paclitaxel combination) (n = 15) No. (%) | Total (N = 36) No. (%) |
|---|---|---|---|---|
| Age, years | | | | |
| Median | 59 | 62 | 58 | 59 |
| Min-max | 30-69 | 33-71 | 38-74 | 30-74 |
| Sex | | | | |
| Male | 6 (54.5) | 8 (80.0) | 8 (53.3) | 22 (61.1) |
| Female | 5 (45.5) | 2 (20.0) | 7 (46.7) | 14 (38.9) |
| ECOG PS | | | | |
| 1 | 11 (100) | 10 (100) | 15 (100) | 36 (100) |
| Site of primary tumor | | | | |
| Gastric | 11 (100) | 9 (90.0) | 15 (100) | 35 (97.2) |
| GEJ | — | 1 (10.0) | — | 1 (2.8) |

TABLE 6-continued

Patient demographics and clinical characteristics.

| | Regimen A (Minnelide mono) (n = 11) No. (%) | Regimen B (Minnelide plus Paclitaxel combination) (n = 10) No. (%) | Regimen C (Minnelide plus Paclitaxel combination) (n = 15) No. (%) | Total (N = 36) No. (%) |
|---|---|---|---|---|
| WHO histology, n (%) | | | | |
| Adenocarcinoma, MD | 4 (36.4) | 4 (40.0) | 7 (46.7) | 15 (41.7) |
| Adenocarcinoma PD | 6 (54.5) | 5 (50.0) | 4 (26.7) | 15 (41.7) |
| Poorly cohesive carcinoma or Signet ring cell carcinoma | | 1 (10.0) | 2 (13.3) | 3 (8.3) |
| Mucinous adenocarcinoma | 1 (9.1) | | | 1 (2.8) |
| Unclassified | | | 2 (13.3) | 2 (5.6) |
| $^a$EBV status | | | | |
| Positive | — | — | — | — |
| Negative | 9 (100) | 8 (100) | 13 (100) | 30 (100) |
| HER2 status | | | | |
| Positive | 2 (18.2) | 1 (10.0) | 3 (20.0) | 6 (16.7) |
| Negative | 9 (81.8) | 9 (90.0) | 12 (80.0) | 30 (83.3) |
| $^b$PD-L1 status | | | | |
| Positive | 4 (80.0) | 7 (87.5) | 8 (66.7) | 19 (76.0) |
| Median CPS (range) | 11.5 (1-70) | 10 (1-20) | 3 (1-90) | 5 (1-90) |
| Negative | 1 (20.0) | 1 (12.5) | 4 (33.3) | 6 (24.0) |
| $^c$TMB status | | | | |
| High | 1 (25.0) | 1 (12.5) | 1 (8.3) | 3 (12.5) |
| Low | 3 (75.0) | 7 (87.5) | 11 (91.7) | 21 (87.5) |
| $^d$MSI status | | | | |
| MSI-high | — | — | — | — |
| MSS | 8 (100) | 9 (100) | 12 (92.3) | 29 (96.7) |
| Indeterminate | | | 1 (7.7) | 1 (3.3) |
| Previous lines of therapy | | | | |
| Median | 3 | 3 | 2 | 3 |
| Min-max | 1-6 | 2-5 | 1-5 | 1-6 |
| Previous IO therapy | | | | |
| Yes | 4 (36.4) | 3 (30.0) | 8 (53.3) | 15 (41.7) |
| No | 7 (63.6) | 7 (70.0) | 7 (46.7) | 21 (58.3) |
| Previous Paclitaxel | | | | |
| Yes | NA | 8 (80.0) | 8 (53.3) | NA |
| No | NA | 2 (20.0) | 7 (46.7) | NA |
| Prior gastrectomy | | | | |
| Curative intent | 7 (63.6) | 1 (10.0) | 6 (40.0) | 14 (38.9) |
| Palliative intent | 1 (9.1) | 1 (10.0) | 3 (20.0) | 5 (13.9) |
| None | 3 (27.3) | 8 (80.0) | 6 (40.0) | 17 (47.2) |

Abbreviations: BSA, body surface area; ECOG, Eastern Cooperative Oncology Group; GEJ, gastroesophageal junction; max, maximum; min, minimum; WHO, World Health Organization; HER2, human epidermal growth factor receptor 2; EBV, Epstein-Barr virus; MSI, microsatellite instability; NA, not applicable.
$^a$Missing EBV status data for 2 in cohort A, 2 in cohort B and 2 in cohort C (total 6 patients);
$^b$Missing PD-L1 status for 6 in cohort A, 2 in cohort B and 3 in cohort C (total 11 patients);
$^c$Missing TMB status for 7 in cohort A, 2 in cohort B and 3 in cohort C (total 12 patients);
$^d$Missing MSI status for 3 in cohort A, 1 in cohort B and 2 in cohort C (total 6 patients).

At data cutoff date (Dec. 20, 2023), 32 patients (89%) had discontinued study treatment, and 4 patients were still undergoing treatment. The primary reason for discontinuation was progressive disease. Five patients (2 in Regimen A, 2 in Regimen B, 1 in Regimen C) did not complete cycle 1 (FIG. 4) and the number of evaluable subjects for safety and antitumor activity was 36 and 31, respectively.

Safety. There were two dose-limiting toxicities (DLTs) in Minnelide Prodrug Monotherapy Regimen A (Dose level 3 minnelide prodrug 1.5 mg: Grade 3 abdominal pain). No DLTs occurred in minnelide prodrug plus paclitaxel combination treatment. The most common treatment-related AEs (TRAEs) were anorexia (18/36, 50%), abdominal pain (16/36, 44.4%), nausea (12/36, 33.3%) and neutropenia (11/36, 30.6%) (Table 7). The majority of TRAEs were grade 1 or 2. TRAEs above Grade 3 occurred in 16 patients (44.4%); neutropenia (19.4%) was most common followed by abdominal pain (11.1%). There were four Grade 5 AEs caused by gastric cancer progression.

TABLE 7

Treatment-related adverse events (TRAEs).

| Adverse events, n (%) | Regimen A Minnelide mono (n = 11) Any/≥Gr 3 | Regimen B Minnelide + Paclitaxel (n = 10) Any/≥Gr 3 | Regimen C Minnelide + Paclitaxel (n = 15) Any/≥Gr 3 | Total (n = 36) Any/≥Gr 3 |
|---|---|---|---|---|
| Overall | 11 (100.0)/8 (72.7) | 9 (90.0)/3 (30.0) | 14 (93.3)/5(33.3) | 34 (94.4)/16 (44.4) |
| Nausea | 6 (54.5)/2 (18.2) | 3 (30.0)/— | 3 (20.0)/— | 12 (33.3)/2(5.6) |
| Anorexia | 8 (72.7)/— | 4 (40.0)/— | 6 (40.0)/— | 18 (50.0)/— |
| Vomiting | 3 (27.3)/1 (9.1) | 1 (10.0)/— | 1 (6.7)/— | 5 (13.9)/1 (2.8) |
| Constipation | 1 (9.1)/— | 1 (10.0)/— | 1 (6.7)/— | 3 (8.3)/— |
| Abdominal pain | 5 (45.5)/2 (18.2) | 4 (40.0)/— | 7 (46.7)/2 (13.3) | 16 (44.4)/4 (11.1) |
| General weakness | — | 2 (20.0)/— | — | 2 (5.6)/— |
| Fatigue | 3 (27.3)/— | 1 (10.0)/— | 3 (20.0)/— | 7 (19.4)/— |
| Weight loss | — | 1 (10.0)/— | — | 1 (2.8)/— |
| Pruritus | — | 1 (10.0)/— | — | 1 (2.8)/— |
| Rash | — | — | 1 (6.7)/— | 1 (2.8)/— |
| Headache | — | — | 1 (6.7)/— | 1 (2.8)/— |
| Mucositis | — | — | 1 (6.7)/— | 1 (2.8)/— |
| Edema | — | — | 1 (6.7)/— | 1 (2.8)/— |
| Cancer pain | 3 (27.3)/1 (9.1) | — | — | 3 (8.3)/1 (2.8) |
| Cancer progression | 3 (27.3)/3 (27.3) | 1 (10)/1 (10) | — | 4 (11.1)/4 (11.1) |
| Dyspepsia | 1 (9.1)/— | 1 (10.0)/— | — | 2 (5.6)/— |
| Gastric stenosis | 1 (9.1)/1 (9.1) | — | — | 1 (2.8)/1 (2.8) |
| Sore throat | — | — | 1 (6.7)/— | 1 (2.8)/— |
| Dysuria | 1 (9.1)/— | — | — | 1 (2.8)/— |
| Urinary tract infection | 1 (9.1)/— | 1 (10.0)/— | — | 2 (5.6)/— |
| Tachycardia | 1 (9.1)/— | 1 (10.0)/— | — | 2 (5.6)/— |
| Tuberculosis | — | — | 1 (6.7)/— | 1 (2.8)/— |
| Alopecia | — | — | 2 (13.3)/— | 2 (5.6)/— |
| Annualar scaly plaques | 1 (9.1)/— | — | — | 1 (2.8)/— |
| Decreased vision | 1 (9.1)/— | — | — | 1 (2.8)/— |
| Depression | 1 (9.1)/— | — | — | 1 (2.8)/— |
| Azotemia | 1 (9.1)/— | 1 (10.0)/— | — | 2 (5.6)/— |
| Neutropenia | 1 (9.1)/1 (9.1) | 3 (30.0)/1(10.0) | 7 (46.7)/5 (33.3) | 11 (30.6)/7 (19.4) |
| Anemia | 2 (18.2)/2 (18.2) | 1 (10.0)/1 (10) | 2 (13.3)/— | 5 (13.9)/3 (8.3) |
| Jaundice | — | 1 (10.0)/1 (10) | — | 1 (2.8)/1 (2.8) |
| Hypercalcemia | — | — | 1 (6.7)/1 (6.7) | 1 (2.8)/1 (2.8) |
| Hypophosphatemi | 1 (9.1)/1 (9.1) | — | — | 1 (2.8)/1 (2.8) |

Minnelide prodrug related adverse events (AEs) are summarized in Table 8. The maximum tolerated dose (MTD) was minnelide prodrug 1.25 mg PO once daily for 21 days every 4 weeks as monotherapy. The most common minnelide prodrug-related treatment AEs experienced by patients were anorexia (54.5%), nausea (45.5%) and abdominal pain (27.3%) in Regimen A. In combination treatment Regimen (B&C), abdominal pain (44.0%) and neutropenia (40.0%) were most frequently occurred. Grade ≥3 severity TRAEs were nausea (18.2%), vomiting (9.1%), abdominal pain (18.2%) and neutropenia (9.1%) in minnelide prodrug monotherapy group, whereas 8.0% of patients experienced grade ≥3 abdominal pain and 24.0% of patients with grade ≥3 neutropenia in combination treatment (Table 8).

TABLE 8

Minnelide-related adverse events.

| Adverse events, n (%) | Regimen A Minnelide mono (n = 11) Any/≥Gr 3 | Regimen B Minnelide + Paclitaxel (n = 10) Any/≥Gr 3 | Regimen C Minnelide + Paclitaxel (n = 15) Any/≥Gr 3 | Total (n = 36) Any/≥Gr 3 |
|---|---|---|---|---|
| Overall | 8 (72.7)/4 (11.1) | 7 (70.0)/1 (10.0) | 12 (80.0)/5(33.3) | 27 (75.0)/10 (27.8) |
| Nausea | 5 (45.5)/2 (18.2) | 2 (20.0)/— | 3 (20.0)/— | 10 (27.8)/2(5.6) |
| Anorexia | 6 (54.5)/— | 3 (30.0)/— | 6 (40.0)/— | 15 (41.7)/— |
| Vomiting | 1 (9.1)/1 (9.1) | 1 (10.0)/— | 1 (6.7)/— | 3 (8.3)/— |
| Constipation | — | — | 1 (6.7)/— | 1 (2.8)/— |
| Abdominal pain | 3 (27.3)/2 (18.2) | 4 (40.0)/— | 7 (46.7)/2 (13.3) | 14 (38.9)/4 (11.1) |
| General weakness | — | 1 (10.0)/— | — | 1 (2.8)/— |
| Fatigue | 2 (18.2)/— | — | 2 (13.3)/— | 4 (11.1)/— |
| Pruritus | — | 1 (10.0)/— | — | 1 (2.8)/— |
| Neutropenia | 1 (9.1)/1 (9.1) | 3 (30.0)/1(10.0) | 7 (46.7)/5 (33.3) | 11 (30.5)/7 (19.4) |

Figure 5A:
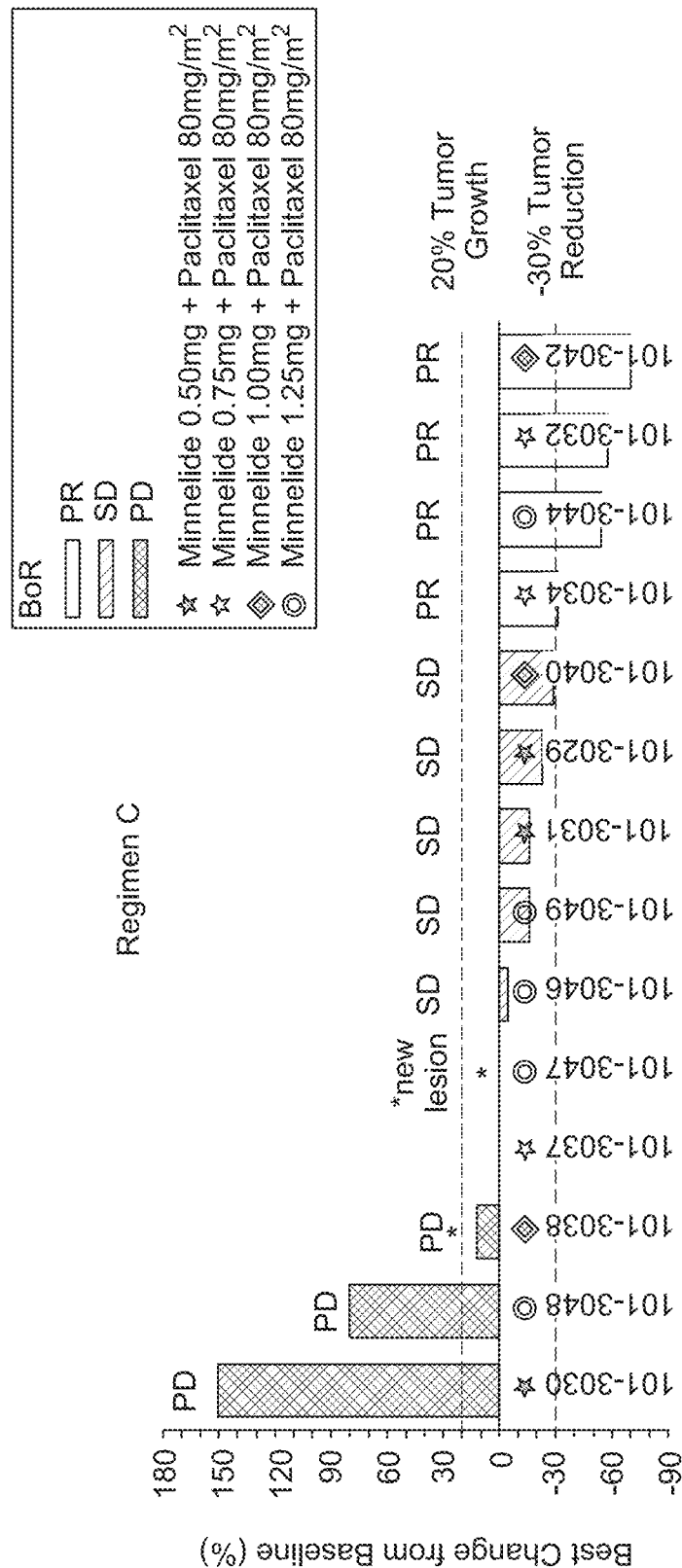
FIG. 5A. Regimen C: Best percentage change in tumor size from baseline. Each bar represents an individual patient. "Best change from baseline" represents the change in the sum of tumor diameters for target lesions. BOR, best overall response; PD, progressive disease; PR, partial response; SD, stable disease.
Figure 8:
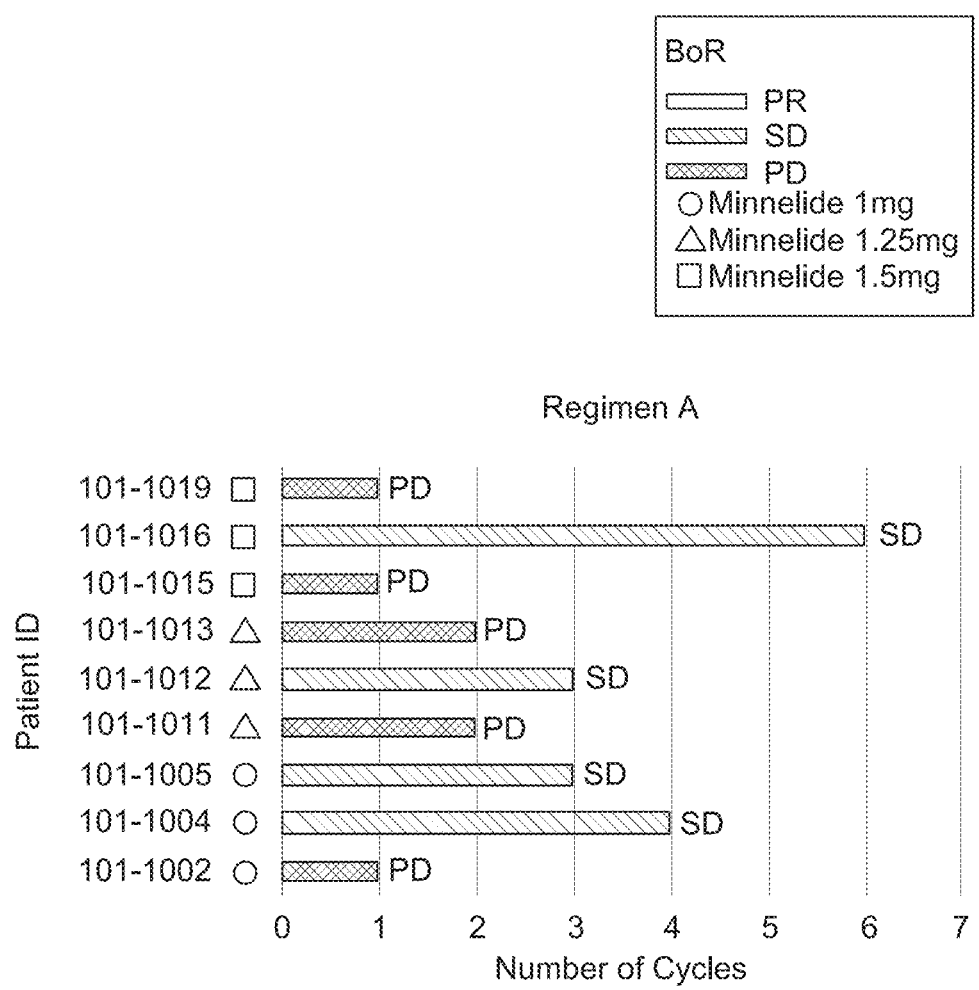
FIG. 8. Regimen A results for number of cycles per patient and best percentage change in tumor size from baseline.
Figure 8:
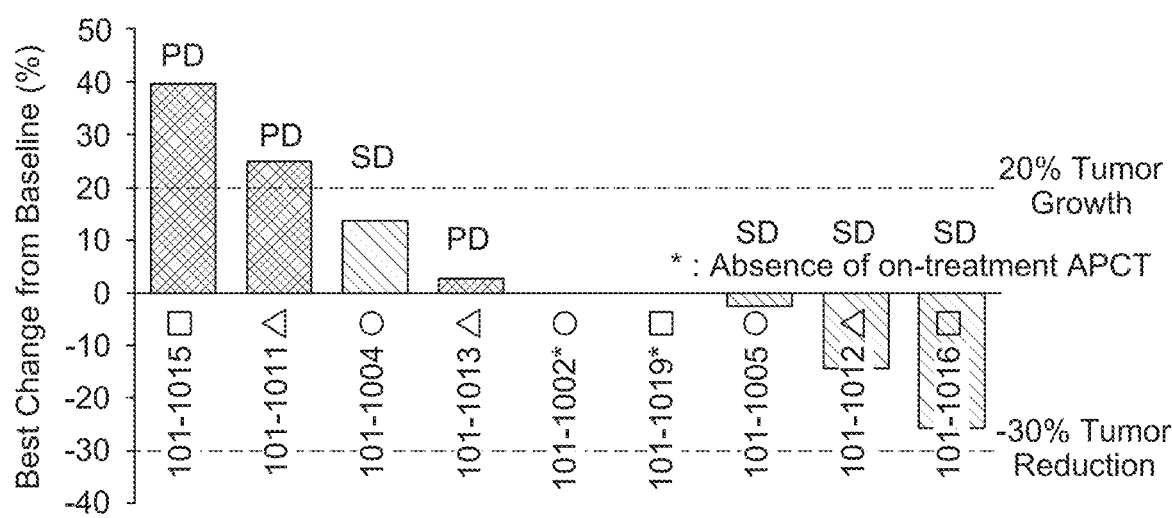

Antitumor activity. In Combination Regimen C, four patients (28.6%) showed Partial Response (PR) and six patients (42.9%) showed Stable Disease (SD) (FIG. 5A). Four patients experienced a stable disease (44.4%) in Regimen A and three patients (37.5%) in Regimen B. In Regimen A (Monotherapy) nine patients who completed at least 1 cycle of treatment with measurable lesions, the BOR was SD (44.4%) or PD (55.6%). DCR was 44.4% (95% CI 13.7-78.8) (FIG. 8) (Table 9 and Table 10).

TABLE 9

Overall response outcome in Regimen A.

| | Minnelide prodrug mono<br>n = 11 |
|---|---|
| [a]BOR | |
| CR | |
| PR | |
| SD | 4 |
| PD | 5 |
| NE | 2 |
| ORR, n (%) | 0 |
| 95% CI (%) | |
| DCR, n (%) | 4 (36.4) |
| 95% CI (%) | 10.9-69.2 |

Abbreviations: BOR, best overall response; CI, confidence interval; CR, complete response; DCR, disease control rate; NE, not evaluable; ORR, objective response rate; PD, progressive disease; PR, partial response; RECIST v1.1, response evaluation criteria in solid tumors version 1.1; SD, stable disease.
[a]The definition of BOR followed RECIST v1.1. CR/PR had to be confirmed by two scans ≥4 weeks apart. When SD was believed to be the BOR, the assessment had to be at least 6-8 weeks from the first IP administration date.
[c]Using the exact method based on binomial distribution (Clopper-Pearson).
[d]DCR was defined as the proportion of patients who had a BOR of CR, PR, or SD of ≥4 weeks.

TABLE 10

Summary of progression-free and overall survival in Regimen A.

| | Regimen A: Minnelide mono |
|---|---|
| PFS events, n (%) | 9 |
| Duration of PFS (months)[a] | |
| Median (95% CI) | 1.6 (0.7-2.5) |
| Range | 0.7-5.4 |
| Duration of OS (months)[a] | |
| Median (95% CI) | 5.3 (0.0-13.2) |
| Range | 1.6-11.1 |
| Follow-up time (months) [b] | |
| Median | NE (NE-NE) |

Abbreviations: CI, confidence interval; NE, not estimable; OS, overall survival; PFS, progression-free survival.
[a]Based on Kaplan-Meier estimate.
[b] Based on reverse Kaplan-Meier estimate.

Figure 5B:
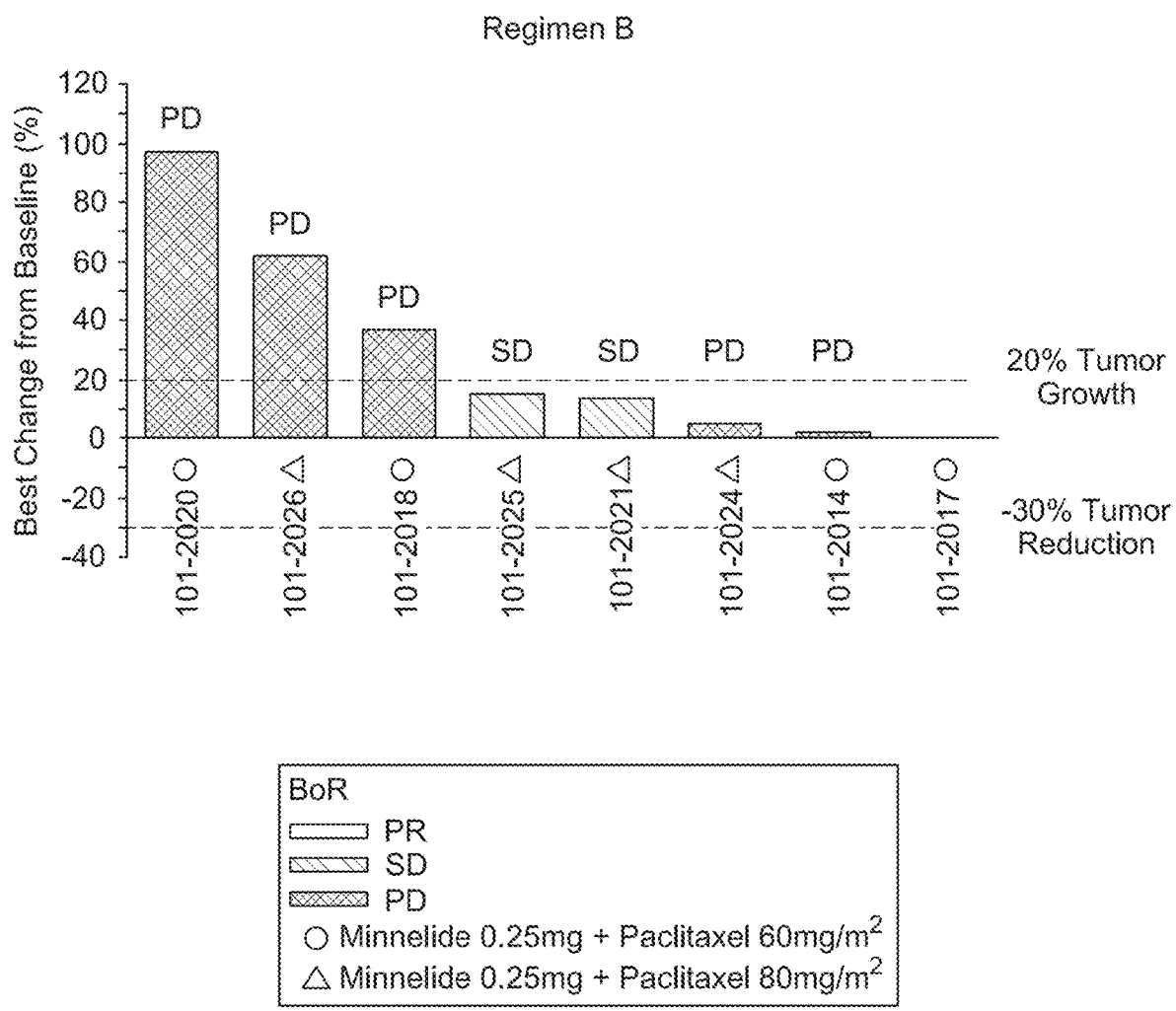
FIG. 5B. Regimen B: Best percentage change in tumor size from baseline. Each bar represents an individual patient. "Best change from baseline" represents the change in the sum of tumor diameters for target lesions. BOR, best overall response; PD, progressive disease; PR, partial response; SD, stable disease.

In Regimen B, eight patients who completed at least 1 cycle of treatment with measurable lesions, the BOR was SD (37.5%) or PD (62.5%) (FIG. 5B). DCR was 37.5% (95% CI 8.5-75.5). In Regimen C, 14 patients who completed at least one cycle of treatment with measurable lesions, the BOR was PR (28.6%), SD (42.9%) or PD (28.6%). The ORR was 28.6% (95% CI 8.4-58.1) and DCR was 71.4% (95% CI 41.9-91.6) (Table 11).

TABLE 11

Overall response outcome in patients that completed Cycle ONE.

| | Regimen B<br>Minnelide +<br>Paclitaxel<br>n = 8 | Regimen C<br>Minnelide +<br>Paclitaxel<br>n = 14 |
|---|---|---|
| [a]BOR | | |
| CR | | |
| PR | | 4 |
| SD | 3 | 6 |
| PD | 5 | 4 |
| ORR, n (%) | 0 | 4 (28.6) |
| 95% CI (%) | | 8.4-58.1 |
| DCR, n (%) | 3 (37.5%) | 10 (71.4) |
| 95% CI (%) | 8.5-75.5 | 41.9-91.6 |

Abbreviations: BOR, best overall response; CI, confidence interval; CR, complete response; DCR, disease control rate; ORR, objective response rate; PD, progressive disease; PR, partial response; RECIST v1.1, response evaluation criteria in solid tumors version 1.1; SD, stable disease.
[a]The definition of BOR followed RECIST v1.1. CR/PR had to be confirmed by two scans ≥4 weeks apart. When SD was believed to be the BOR, the assessment had to be at least 6-8 weeks from the first IP administration date.
[c]Using the exact method based on binomial distribution (Clopper-Pearson).
[d]DCR was defined as the proportion of patients who had a BOR of CR, PR, or SD of ≥4 weeks.

Figure 6A:
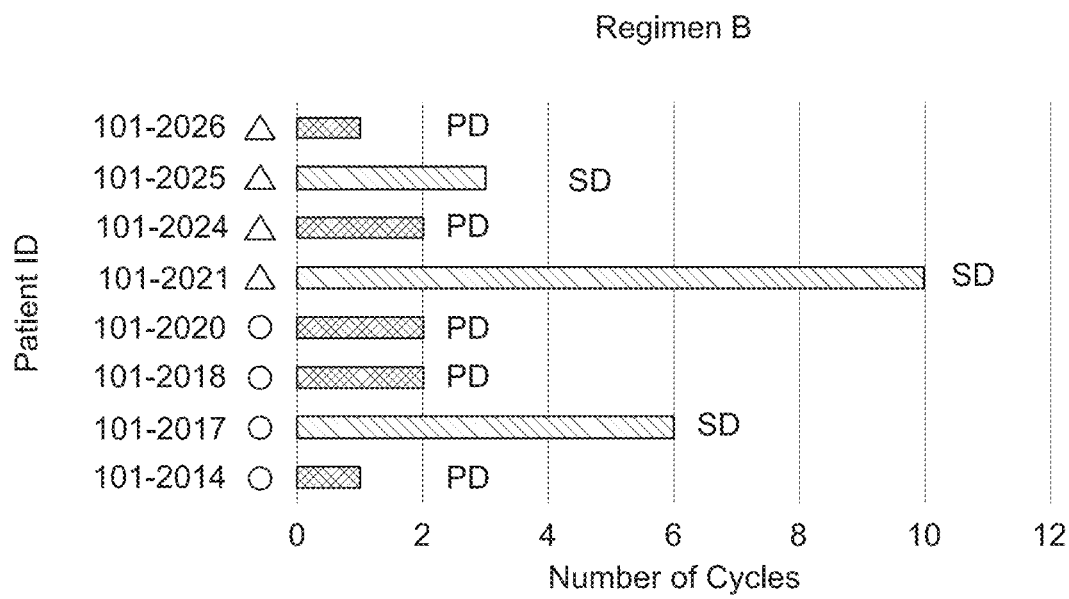
FIG. 6A. Regimen B treatment exposure and response of duration based on investigator assessment as per RECIST v1.1.
Figure 6A:
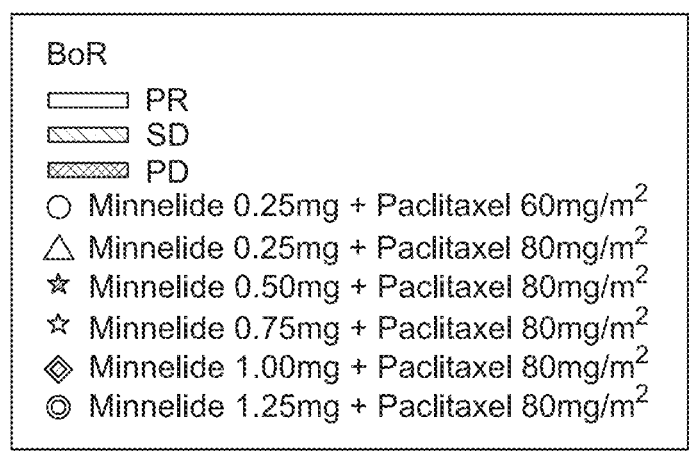
Figure 6B:
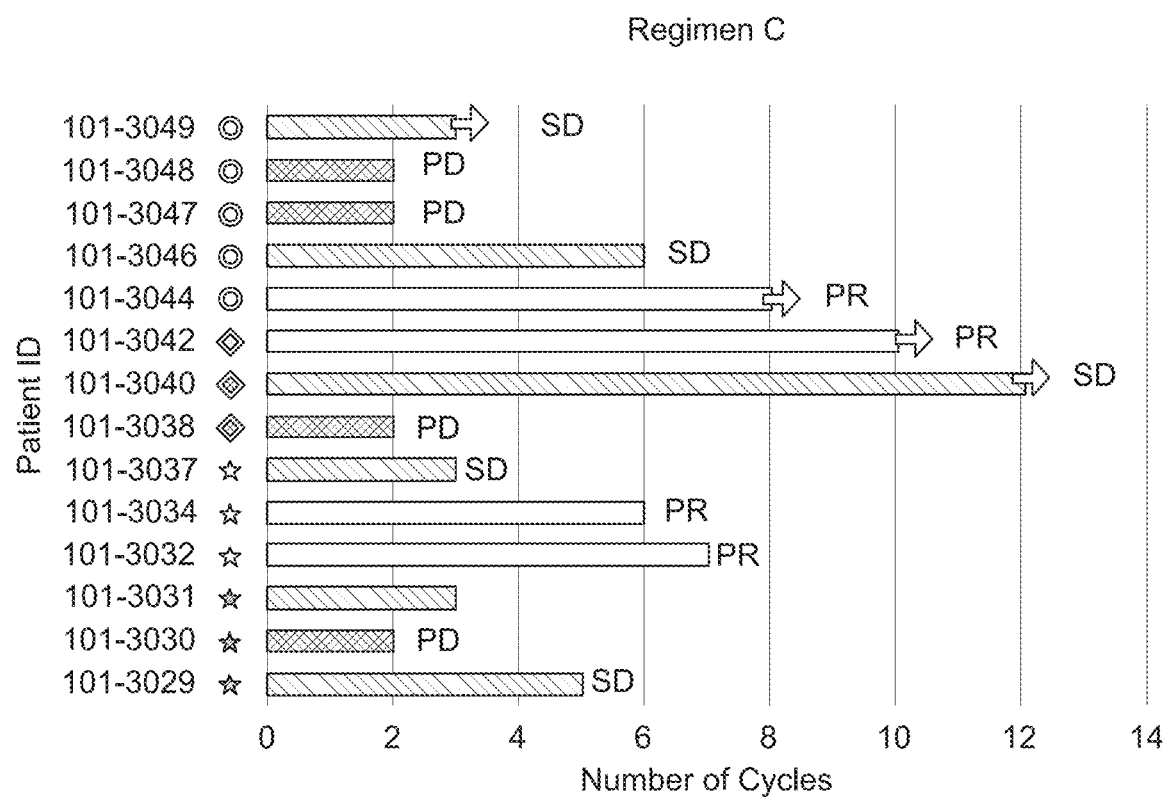
FIG. 6B. Regimen C treatment exposure and response of duration based on investigator assessment as per RECIST v1.1.
Figure 6B:
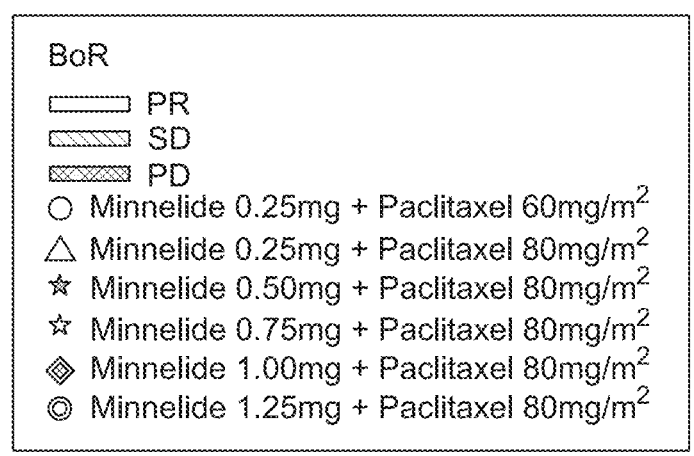

In Regimen B, two patients had SD ≥6 months (FIG. 6A). Among 6 patients showing SD in Regimen C, one patient received paclitaxel 80 mg/m$^2$+Minnelide 1.0 mg/d had prolonged stable disease over 1 year with reduction in tumor size (FIG. 6B). Two patients experienced prolonged PR (≥8 months). Four patients are still undergoing paclitaxel plus Minnelide treatment at time of submission.

The median PFS was 1.6 months (95% CI 0.7-2.5) in Regimen A, 1.6 months (95% CI 1.2-2.0) in Regimen B and 4.5 months (95% CI 0.2-8.8) in Regimen C. The median OS was 5.3 months (95% CI 0.0-13.2) in Regimen A, 4.5 months (95% CI 1.2-7.8) in Regimen B and 10.7 months (95% CI 6.9-14.5) in Regimen C (Table 12).

TABLE 12

Summary of progression-free and overall survival: patients that completed Cycle ONE.

| | Regimen B<br>Minnelide + Paclitaxel<br>n = 8 | Regimen C<br>Minnelide + Paclitaxel<br>n = 14 |
|---|---|---|
| PFS events, n (%) | 8 | 10 |
| Duration of PFS (months)[a] | | |
| Median (95% CI) | 1.6 (1.2-2.0) | 4.5 (0.2-8.8) |
| Range | 0.8-5.5 | 1.6-8.2 |
| Duration of OS (months)[a] | | |
| Median (95% CI) | 4.5 (1.2-7.8) | 10.7 (6.9-14.5) |
| Range | 2.2-22.4 | 2.1-14.3 |

Abbreviations: CI, confidence interval; NE, not estimable; OS, overall survival; PFS, progression-free survival;
[a]Based on Kaplan-Meier estimate.
[b] Based on reverse Kaplan-Meier estimate.

In Regimen B, the median PFS was 1.3 months (95% CI 0.84-1.76) for patients who were previously treated with paclitaxel (n=8) and 1.6 months (95% CI NE-NE) for patients without previous exposure to paclitaxel (n=2) (p=0.266). The median OS was 3.6 months (95% CI 1.66-5.54) for patients who were previously treated with paclitaxel (n=8) and 4.5 months (95% CI NE-NE) for patients without previous exposure to paclitaxel (n=2) (p=0.569).

In Regimen C, the median PFS and OS were 2.4 months (95% CI 0.68-4.12) and 8.3 months (95% CI 0.00-18.05) for patients who were previously treated with paclitaxel (n=8), respectively. Among the patients without previous exposure to paclitaxel (n=7), the median PFS and OS were 5.4 months (95% CI 5.20-5.61) and 14.3 months (95% CI NE-NE) (p=0.295 for PFS; p=0.301 for OS. Among the patients without previous exposure to paclitaxel (n=4) in the last 2 cohorts of Regimen C, three had a confirmed ORR of 50.0%, DCR of 75.0%, and the median PFS was 5.3 months and the median OS was not reached.

Figure 7:
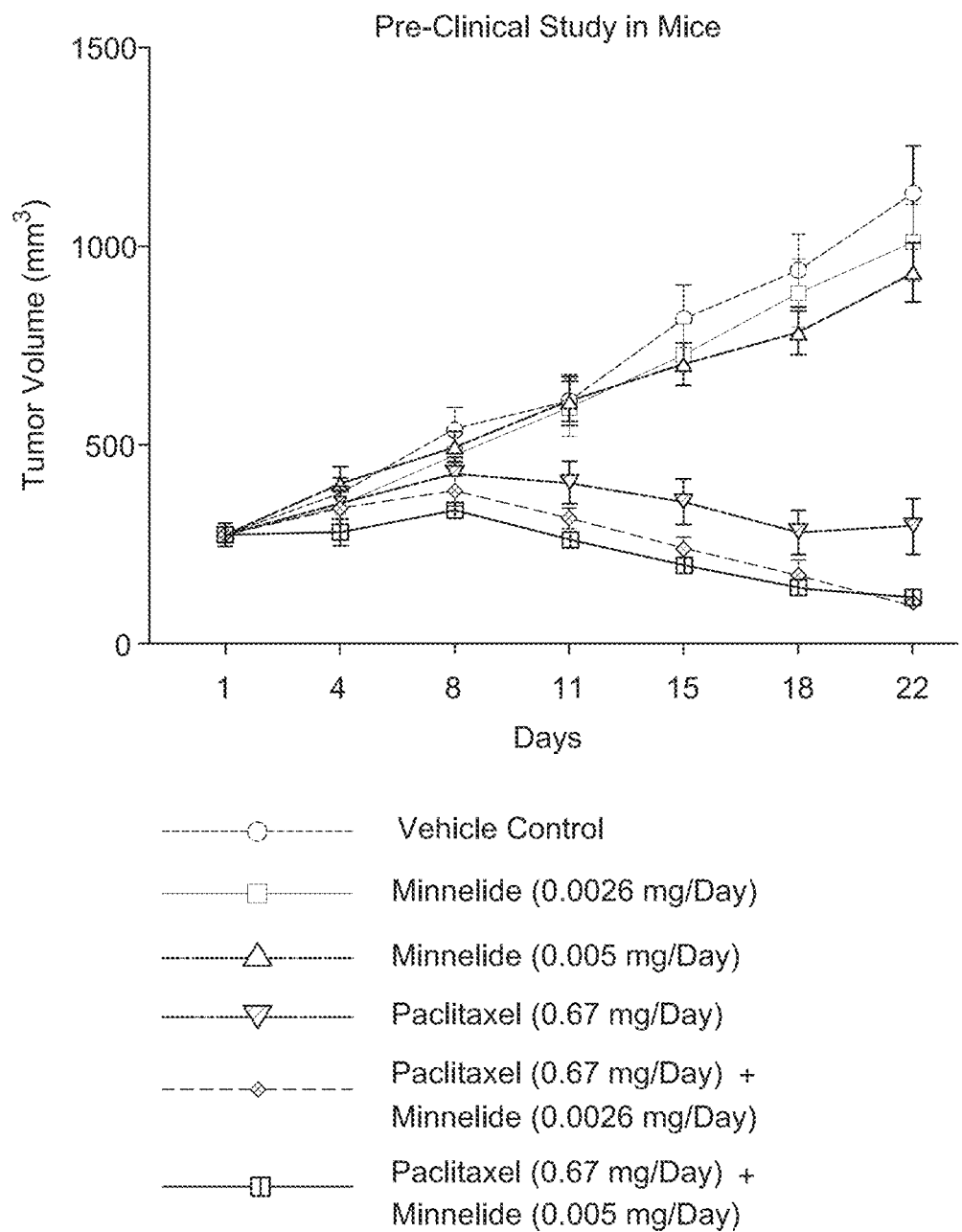
FIG. 7. Graph of results from pre-clinical study in mice showing tumor volume (mm$^3$) increase or decrease from days 1 to 22.

Significantly, FIG. 5A illustrates the Regimen C synergy of minnelide prodrug when administered in combination with paclitaxel where 11 of 14 patients showed at least a 20% reduction in tumor growth and nine had a reduction of tumor size, with five of those nine showing a significant reduction in tumor size (30-60%). This striking synergy is also shown in FIG. 7 (graphical results of a pre-clinical study in mice), which illustrates (a) the control subjects receiving a vehicle, and test mice receiving minnelide prodrug alone at (b) 0.0026 mg/day and (c) 0.005 mg/day, and (d) paclitaxel alone in comparison to (e) 0.0026 mg/day minnelide prodrug in combination with 0.67 mg/day paclitaxel and (f) 0.005 mg/day minnelide prodrug in combination with 0.67 mg/day paclitaxel.

Discussion

This phase 1 study evaluated the safety and efficacy of oral minnelide prodrug monotherapy and minnelide prodrug plus paclitaxel combination therapy in Korean patients with locally advanced or metastatic gastric cancer who had previously received multiple lines of therapy. Two DLTs occurred at a dose of 1.5 mg of minnelide prodrug monotherapy, and minnelide prodrug 1.25 mg was confirmed as the MTD. No DLTs were observed in patients treated with minnelide prodrug plus paclitaxel and combination treatment was well tolerated.

Most treatment-related AEs with minnelide prodrug were anorexia, abdominal pain, neutropenia and nausea. Grade 3 or higher AEs with minnelide prodrug occurred in 27.8% overall, followed by neutropenia (19.4%), abdominal pain (11.1%) and nausea (5.6%). No significant difference between previous gastrectomy and the occurrence of abdominal pain AE was observed. The overall TRAEs types and incidence rates were similar to minnelide prodrug-related AEs. The majority of TRAEs were grade 1 or 2 and the most common TRAEs were anorexia (18/36, 50%), abdominal pain (16/36, 44.4%), nausea (12/36, 33.3%) and neutropenia (11/36, 30.6%). Four grade 5 AEs caused by gastric cancer progression were reported (3 in Regimen A, 1 in Regimen B).

Although objective responses were not observed with single-agent minnelide prodrug, some patients experienced tumor shrinkage who previously received at least two lines of chemotherapy. One patient who had previously failed four lines of therapy including immunotherapy showed a stable disease for 5.4 months.

The addition of paclitaxel with minnelide prodrug was shown to improve response rate and provide prolonged PFS and OS compared with minnelide prodrug alone. Especially in Regimen C, minnelide prodrug plus paclitaxel demonstrated promising antitumor activity with confirmed ORR of 28.6%, DCR of 71.4%; the median PFS was 4.5 months (95% CI 0.2-8.8) and the median OS was 10.7 months (95% CI 6.9-14.5). This is comparable to the median PFS of 4.4 months and OS of 9.6 months of paclitaxel plus ramucirumab, which is currently the most used second-line standard treatment for AGC.

Furthermore, minnelide prodrug in combination with paclitaxel (Regimen B and C) showed 43.8% (7/16) of disease control rate among patients previously treated with paclitaxel (n=16). These findings indicate that administering minnelide prodrug in combination with paclitaxel can overcome resistance to paclitaxel and reverse sensitivity, as reported in a previous study (Wang et al., *J. Clin. Oncol.* 32 (2014)).

The results of this phase 1 study are limited by the poor prognosis of the study population, with many patients having received multiple prior chemotherapy.

To our knowledge, this is the first study of minnelide prodrug with and without paclitaxel for the treatment of patients with AGC who had disease progression on previous lines of therapy. The oral administration of minnelide prodrug alone at a dose of 1.25 mg demonstrated tolerability with restricted single-agent efficacy. Additionally, the combination of minnelide prodrug and paclitaxel as salvage therapy in patients with AGC exhibited meaningful clinical efficacy alongside a manageable safety profile. These data support the use of minnelide prodrug alone and in combination with paclitaxel and/or chemotherapy and immunotherapy in cancer, especially advanced gastric cancer.

The following paragraphs enumerated consecutively from 1 through 15 provide for various additional aspects of the present invention. In one embodiment, in a first paragraph, this disclosure provides:

1. A method for treating gastric cancer in a cancer subject, the method which comprises administering to the cancer subject during a 28 day cycle a therapeutically effective combination of: a) about 0.25 mg to about 2.0 mg of minnelide according to a first regimen wherein a dose is given once per day on days 1 to 5, 8 to 12, and 15 to 19 of the cycle; and
    b) about 60 mg/m$^2$ to about 80 mg/m$^2$ of paclitaxel according to a second regimen wherein a dose is given once per day on days 1, 8, and 15 of the cycle; wherein the 28-day cycle is repeated one or more times and the combination effectively treats the gastric cancer.
2. The method of paragraph 1, wherein the cancer subject is administered about 0.5 mg to about 0.75 mg of minnelide according to the first regimen.
3. The method of paragraphs 1-2, wherein the cancer subject is administered about 0.5 mg of minnelide according to the first regimen and about 60-80 mg/m$^2$ of paclitaxel according to the second regimen.
4. The method of any one of paragraphs 1-3, wherein the cancer subject is administered about 0.25 mg of minnelide according to the first regimen and about 70-90 mg/m$^2$ (e.g., about 80 mg/m$^2$) of paclitaxel according to the second regimen.
5. The method of any one of paragraphs 1-4, wherein the cancer subject is administered about 0.50 mg of minnelide according to the first regimen and about 70-90 mg/m$^2$ (e.g., about 80 mg/m$^2$) of paclitaxel according to the second regimen.
6. The method of any one of paragraphs 1-5, wherein the cancer subject is administered about 0.75 mg of minnelide according to the first regimen and about 70-90 mg/m$^2$ (e.g., about 80 mg/m$^2$) of paclitaxel according to the second regimen.
7. The method of any one of paragraphs 1-6, wherein the cancer subject is administered about 1 mg of minnelide according to the first regimen and about 70-90 mg/m$^2$ (e.g., about 80 mg/m$^2$) of paclitaxel according to the second regimen.

8. The method of any one of paragraphs 1-7, wherein the cancer subject is administered about 1.25 mg of minnelide according to the first regimen and about 70-90 mg/m$^2$ (e.g., about 80 mg/m$^2$) of paclitaxel according to the second regimen.

9. The method of any of paragraphs 1-8, wherein minnelide is administered orally.

10. The method of any of paragraphs 1-9, wherein paclitaxel is administered intravenously.

11. The method of any one of paragraphs 1-10 wherein the cancer patient has tumors that continued to progress after receiving paclitaxel chemotherapy; and/or cancer tumors of the cancer patient are reduced in diameter by 30% or greater after five or more 28-day cycles.

12. The method of any one of paragraphs 1-11 wherein the subject is further suffering from advanced gastric cancer, ovarian cancer, breast cancer, bladder cancer, skin cancer, or a combination thereof, and the method effectively treats the cancer subject.

13. The method of any one of paragraphs 1-12, wherein the cancer subject is a human.

14. The method of any one of paragraphs 1-13, wherein the combination effectively treats the gastric cancer without causing a complete blood count of the cancer subject to lower by more than 25% from baseline.

15. The method of any one of paragraphs 1-14, wherein the combination effectively treats the gastric cancer without causing a platelet count or an absolute neutrophil count in the cancer subject to lower by more than 25% from baseline.

While specific embodiments have been described above with reference to the disclosed embodiments and examples, such embodiments are only illustrative and do not limit the scope of the invention. Changes and modifications can be made in accordance with ordinary skill in the art without departing from the invention in its broader aspects as defined in the following claims.

All publications, patents, and patent documents are incorporated by reference herein, as though individually incorporated by reference. No limitations inconsistent with this disclosure are to be understood therefrom. The invention has been described with reference to various specific and preferred embodiments and techniques. However, it should be understood that many variations and modifications may be made while remaining within the spirit and scope of the invention.

What is claimed is:

1. A method for treating gastric cancer in a cancer patient, the method comprising administering to a gastric cancer patient during a 28 day cycle a therapeutically effective combination of:
   a) about 0.25 mg to about 2.0 mg of minnelide according to a first regimen wherein a dose is given once per day on days 1 to 5, 8 to 12, and 15 to 19 of the cycle; and
   b) about 60 mg/m$^2$ to about 100 mg/m$^2$ of paclitaxel according to a second regimen wherein a dose is given once per day on days 1, 8, and 15 of the cycle;
   wherein the 28-day cycle is repeated one or more times and the combination effectively treats the gastric cancer.

2. The method of claim 1 wherein the cancer patient is administered about 0.5 mg to about 1.25 mg of minnelide according to the first regimen.

3. The method of claim 1 wherein the cancer patient is administered about 0.75mg to about 1.25 mg of minnelide according to the first regimen and about 60 mg/m$^2$ to about 80 mg/m$^2$ of paclitaxel according to the second regimen.

4. The method of claim 1 wherein the cancer patient is administered about 0.75 mg of minnelide according to the first regimen and about 80 mg/m$^2$ of paclitaxel according to the second regimen.

5. The method of claim 1 wherein the cancer patient is administered about 1.0 mg of minnelide according to the first regimen and about 80 mg/m$^2$ of paclitaxel according to the second regimen.

6. The method of claim 1 wherein the cancer patient is administered about 1.25mg of minnelide according to the first regimen and about 80 mg/m$^2$ of paclitaxel according to the second regimen.

7. The method of claim 1 wherein the cancer patient is administered about 1.5 mg of minnelide according to the first regimen and about 80 mg/m$^2$ of paclitaxel according to the second regimen.

8. The method of claim 1 wherein the cancer patient has been diagnosed with advanced gastric cancer.

9. The method of claim 1 wherein the cancer patient has tumors that continued to progress after receiving paclitaxel chemotherapy.

10. The method of claim 1 wherein cancer tumors of the cancer patient are reduced in diameter by 30% or greater after five or more 28-day cycles.

11. The method of claim 1 wherein minnelide is administered orally and paclitaxel is administered intravenously.

12. The method of claim 1 wherein the patient is further suffering from breast cancer, bladder cancer, liver cancer, lung cancer, ovarian cancer, skin cancer, or a combination thereof, and the method effectively treats the cancer patient.

13. The method of claim 1 wherein the combination effectively treats the gastric cancer without causing a complete blood count of the cancer patient to lower by more than 25% from baseline.

14. The method of claim 1 wherein the combination effectively treats the gastric cancer without causing a platelet count or an absolute neutrophil count in the cancer patient to lower by more than 25% from baseline.

15. A method for treating advanced gastric cancer in a cancer patient wherein the cancer continued to progress after paclitaxel chemotherapy, the method comprising administering to the cancer patient diagnosed with advanced gastric cancer during a 28 day cycle a therapeutically effective combination of:
   a) about 0.5 mg to about 1.5 mg of minnelide administered orally according to a first regimen wherein a dose is given once per day on days 1 to 5, 8 to 12, and 15 to 19 of the cycle; and
   b) about 70 mg/m$^2$ to about 90 mg/m$^2$ of paclitaxel administered intravenously according to a second regimen wherein a dose is given once per day on days 1, 8, and 15 of the cycle;
   wherein the 28-day cycle is repeated two or more times, thereby achieving disease stability or disease regression of the advanced gastric cancer.

* * * * *